(12) United States Patent
Quibell et al.

(10) Patent No.: US 6,528,275 B1
(45) Date of Patent: Mar. 4, 2003

(54) SUBSTRATES AND INHIBITORS OF PROTEOLYTIC ENZYMES

(75) Inventors: Martin Quibell, Cambridge (GB); Tony Johnson, Cambridge (GB); Terance Hart, Cambridge (GB)

(73) Assignee: Peptide Therapeutics Limited, Cambridge (GB)

( * ) Notice: Subject to any disclaimer, the term of this patent is extended or adjusted under 35 U.S.C. 154(b) by 0 days.

(21) Appl. No.: 09/171,680

(22) PCT Filed: Apr. 24, 1997

(86) PCT No.: PCT/GB97/01157
§ 371 (c)(1),
(2), (4) Date: Nov. 3, 1999

(87) PCT Pub. No.: WO97/40065
PCT Pub. Date: Oct. 30, 1997

(30) Foreign Application Priority Data

| Apr. 24, 1996 | (GB) | ............................................. 9608457 |
| Jul. 31, 1996 | (GB) | ............................................. 9616115 |
| Nov. 27, 1996 | (GB) | ............................................. 9624584 |

(51) Int. Cl.[7] .......................... C12Q 1/37; G01N 33/53; G01N 33/573; G01N 21/76
(52) U.S. Cl. .............................. 435/23; 435/4; 435/7.6; 435/7.72; 435/DIG. 15; 436/172
(58) Field of Search ........................... 435/4, 7.6, 7.72, 435/23, DIG. 15; 436/172

(56) References Cited

U.S. PATENT DOCUMENTS

| 5,011,910 A | * 4/1991 | Marshall et al. ............. 530/329 |
| 5,164,300 A | 11/1992 | Marshall et al. |
| 5,506,115 A | 4/1996 | Toth et al. |

FOREIGN PATENT DOCUMENTS

| EP | 0 428 000 A1 | 5/1991 |
| WO | WO-91/16336 | * 10/1991 |
| WO | 91/16336 | 10/1991 |
| WO | 93/24517 | 12/1993 |
| WO | WO-94/05394 | * 3/1994 |
| WO | 94/05394 | 3/1994 |
| WO | 94 05394 | 3/1994 |
| WO | 95/16918 | 6/1995 |
| WO | 95/34575 | 12/1995 |
| WO | 95 34575 | 12/1995 |
| WO | 97/25437 | 7/1997 |
| WO | 97 25437 A | 7/1997 |

OTHER PUBLICATIONS

Deprez et al., Sep. 1994, Peptides 1994, Proceedings of the Twenty–Third European Peptide Symposium, pp. 455–456.*
Meldal et al., Apr. 1994, P.N.A.S. 91:3314–3318.*
B. Deprez et al.: "Self–dcifering, orthogonal combinatorial libraries of soluble organic compounds: Discovery of a potent V2 vasopressin antagonist" in: XP0020242096 Peptides 1994 Proceeding of the Twenty–Third European Symposium Sep. 4–10, 1994, Braga, Portugal ed. HLS Maia; pub. ESCOM, Leiden, NL, 1995, pp. 455–456.
Matayoshi et al, "A Rapid Fluorogenic Assay of HIV Protease Inhibitors," pp. 566–568.
Matayoshi et al, "Novel Fluorogenic Substrates for Assaying Retroviral . . . ," Science, vol. 247, pp. 954–958 (1990).
Capobianco et al, "Application of a Fluorogenic Subtrate in the Assay of Proteolytic . . . ," Analytical Biochemistry, vol. 204, pp. 92–102 (1992).
Meldal et al, "Direct visualization of enzyme inhibitors using a portion . . . ," J. Chem. Soc. Perkin Trans., vol. 1, pp. 1591–1596 (1995).
Singh et al, "Validation of Screening Immobilized Peptide . . . ," Journal of Medicinal Chemistry, vol. 38, No. 2, pp. 217–219 (1995).
Meldal et al, "Anthranilamide and Nitrotyrosine as a Donor–Acceptor . . . ," Analytical Biochemistry, vol. 195, pp. 141–147 (1991).
Meldal et al; "Portion–mixing peptide libraries of quenched . . . ," Proc. Natl. Acad. Sci. USA, vol. 91, pp. 3314–3318 (1994).
Williard et al, "Self–decipherin, orthogonal . . . ," Peptides 1994, pp. 455–456.

* cited by examiner

*Primary Examiner*—Padmashri Ponnaluri
*Assistant Examiner*—Tomas Friend
(74) *Attorney, Agent, or Firm*—Nixon & Vanderhye

(57) ABSTRACT

The present invention relates to the field of compounds which are substrates or inhibitors of proteolytic enzymes and to apparatus and methods for identifying substrates or inhibitors for proteolytic enzymes. We have devised a combinatorial method for the rapid indentification of binding motifs which will greatly expedite the synthesis of inhibitors of a variety of proteolytic enzymes such as aspartyl proteases, serine proteases, metallo proteases and cysteinyl proteases.

10 Claims, 14 Drawing Sheets

|    | 1  | 2  | 3  | 4  | 5  | 6  | 7  | 8  | 9  | 10  | 11 | 12 |
|----|----|----|----|----|----|----|----|----|----|-----|----|----|
| A  | A1 | A2 | A3 | A4 | A5 | A6 | A7 | A8 | A9 | A10 |    |    |
| B  | B1 | B2 | B3 | B4 | B5 | B6 | B7 | B8 | B9 | B10 |    |    |
| C  | C1 | C2 | C3 | C4 | C5 | C6 | C7 | C8 | C9 | C10 |    |    |
| D  | D1 | D2 | D3 | D4 | D5 | D6 | D7 | D8 | D9 | D10 |    |    |
| E  | E1 | E2 | E3 | E4 | E5 | E6 | E7 | E8 | E9 | E10 |    |    |
| F  | F1 | F2 | F3 | F4 | F5 | F6 | F7 | F8 | F9 | F10 |    |    |
| G  | G1 | G2 | G3 | G4 | G5 | G6 | G7 | G8 | G9 | G10 |    |    |
| H  | H1 | H2 | H3 | H4 | H5 | H6 | H7 | H8 | H9 | H10 |    |    |

*Figure 1*

First Example of Library Matrix where n=1

Component Distribution in Plate 1, Library 1 (n=1).

|  | C1 | C2 | C3 | C4 | C5 | C6 | C7 | C8 | C9 | C10 |
|---|---|---|---|---|---|---|---|---|---|---|
| D1 | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ |
| D2 | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ |
| D3 | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ |
| D4 | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ |
| D5 | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ |
| D6 | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ |
| D7 | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ |
| D8 | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ |

*Figure 2*

Component Location in Plate 1, Library 2 (n=1).

|    | B1 | B2 | B3 | B4 | B5 | B6 | B7 | B8 | B9 | B10 |
|----|----|----|----|----|----|----|----|----|----|-----|
| E1 | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ |
| E2 | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ |
|    |    |    |    |    |    |    |    |    |    |     |
|    |    |    |    |    |    |    |    |    |    |     |
|    |    |    |    |    |    |    |    |    |    |     |
|    |    |    |    |    |    |    |    |    |    |     |
|    |    |    |    |    |    |    |    |    |    |     |
|    |    |    |    |    |    |    |    |    |    |     |

*Figure 3*

Component Location in Plate 2, Library 2 (n=1).

|    | B1 | B2 | B3 | B4 | B5 | B6 | B7 | B8 | B9 | B10 |
|----|----|----|----|----|----|----|----|----|----|-----|
| E1 | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ |
| E2 | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ |
|    |    |    |    |    |    |    |    |    |    |     |
|    |    |    |    |    |    |    |    |    |    |     |
|    |    |    |    |    |    |    |    |    |    |     |
|    |    |    |    |    |    |    |    |    |    |     |
|    |    |    |    |    |    |    |    |    |    |     |
|    |    |    |    |    |    |    |    |    |    |     |

*Figure 4*

Component Location in Plate 3, Library 2 (n=1).

|    | B1 | B2 | B3 | B4 | B5 | B6 | B7 | B8 | B9 | B10 |
|----|----|----|----|----|----|----|----|----|----|-----|
| E1 | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ |
| E2 | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ |
|    |    |    |    |    |    |    |    |    |    |     |
|    |    |    |    |    |    |    |    |    |    |     |
|    |    |    |    |    |    |    |    |    |    |     |
|    |    |    |    |    |    |    |    |    |    |     |
|    |    |    |    |    |    |    |    |    |    |     |
|    |    |    |    |    |    |    |    |    |    |     |

*Figure 5*

Component Location in Plate 4, Library 2 (n=1).

|    | B1 | B2 | B3 | B4 | B5 | B6 | B7 | B8 | B9 | B10 |
|----|----|----|----|----|----|----|----|----|----|-----|
| E1 | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ |
| E2 | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ |
|    |    |    |    |    |    |    |    |    |    |     |
|    |    |    |    |    |    |    |    |    |    |     |
|    |    |    |    |    |    |    |    |    |    |     |
|    |    |    |    |    |    |    |    |    |    |     |
|    |    |    |    |    |    |    |    |    |    |     |
|    |    |    |    |    |    |    |    |    |    |     |

*Figure 6*

Example Library where n = 4

Component Distribution in Plate 1, Library 1 (n = 4).

|   | C1 | C2 | C3 | C4 | C5 | C6 | C7 | C8 | C9 | C10 |
|---|---|---|---|---|---|---|---|---|---|---|
| D1 | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ |
| D2 | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ |
| D3 | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ |
| D4 | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ |
| D5 | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ |
| D6 | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ |
| D7 | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ |
| D8 | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ | $B_{1-10}$ $E_{1-2}$ |

*Figure 7*

Component Location in Plate 2, Library 1 (n=4).

|    | C1 | C2 | C3 | C4 | C5 | C6 | C7 | C8 | C9 | C10 |
|---|---|---|---|---|---|---|---|---|---|---|
| D1 | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ |
| D2 | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ |
| D3 | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ |
| D4 | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ |
| D5 | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ |
| D6 | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ |
| D7 | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ |
| D8 | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ | $B_{1-10}$ $E_{3-4}$ |

*Figure 8*

Component Location in Plate 3, Library 1 (n=4).

|    | C1 | C2 | C3 | C4 | C5 | C6 | C7 | C8 | C9 | C10 |
|----|----|----|----|----|----|----|----|----|----|-----|
| D1 | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ |
| D2 | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ |
| D3 | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ |
| D4 | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ |
| D5 | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ |
| D6 | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ |
| D7 | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ |
| D8 | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ | $B_{1-10}$ $E_{5-6}$ |

Figure 9

Component Location in Plate 4, Library 1 (n=4).

|    | C1 | C2 | C3 | C4 | C5 | C6 | C7 | C8 | C9 | C10 |
|----|----|----|----|----|----|----|----|----|----|-----|
| D1 | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ |
| D2 | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ |
| D3 | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ |
| D4 | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ |
| D5 | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ |
| D6 | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ |
| D7 | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ |
| D8 | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ | $B_{1-10}$ $E_{7-8}$ |

*Figure 10*

Component Location in Plate 1, Library 2 (n=4).

|    | B1 | B2 | B3 | B4 | B5 | B6 | B7 | B8 | B9 | B10 |
|----|----|----|----|----|----|----|----|----|----|-----|
| E1 | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ |
| E2 | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ |
| E3 | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ |
| E4 | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ |
| E5 | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ |
| E6 | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ |
| E7 | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ |
| E8 | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ | $C_{1-10}$ $D_{1-2}$ |

*Figure 11*

Component Location in Plate 2, Library 2 (n=4).

|    | B1 | B2 | B3 | B4 | B5 | B6 | B7 | B8 | B9 | B10 |
|----|----|----|----|----|----|----|----|----|----|-----|
| E1 | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ |
| E2 | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ |
| E3 | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ |
| E4 | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ |
| E5 | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ |
| E6 | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ |
| E7 | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ |
| E8 | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ | $C_{1-10}$ $D_{3-4}$ |

*Figure 12*

Component Location in Plate 3, Library 2 (n=4).

|    | B1 | B2 | B3 | B4 | B5 | B6 | B7 | B8 | B9 | B10 |
|----|----|----|----|----|----|----|----|----|----|-----|
| E1 | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ |
| E2 | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ |
| E3 | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ |
| E4 | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ |
| E5 | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ |
| E6 | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ |
| E7 | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ |
| E8 | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ | $C_{1-10}$ $D_{5-6}$ |

*Figure 13*

Component Location in Plate 4, Library 2 (n=4).

|     | B1 | B2 | B3 | B4 | B5 | B6 | B7 | B8 | B9 | B10 |
|-----|----|----|----|----|----|----|----|----|----|-----|
| E1  | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ |
| E2  | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ |
| E3  | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ |
| E4  | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ |
| E5  | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ |
| E6  | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ |
| E7  | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ |
| E8  | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ | $C_{1-10}$ $D_{7-8}$ |

*Figure 14*

SEQUENCE LISTING

```
<160> NUMBER OF SEQ ID NOS: 105

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (4)
<223> OTHER INFORMATION: Nle
<221> NAME/KEY: MOD_RES
<222> LOCATION: (6)
<223> OTHER INFORMATION: Tyr(NO2)

<400> SEQUENCE: 1

Xaa Val Ala Xaa Ser Xaa Asp
 1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: Nle
<221> NAME/KEY: MOD_RES
<222> LOCATION: (5)
<223> OTHER INFORMATION: Tyr(NO2)

<400> SEQUENCE: 2

Val Ala Xaa Ser Xaa Asp
 1               5
```

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: Nle
<221> NAME/KEY: MOD_RES
<222> LOCATION: (4)
<223> OTHER INFORMATION: Tyr(NO2)

<400> SEQUENCE: 3

Ala Xaa Ser Xaa Asp
 1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: Nle
<221> NAME/KEY: MOD_RES
<222> LOCATION: (5)
<223> OTHER INFORMATION: Tyr(NO2)

<400> SEQUENCE: 4

Val Ala Xaa Ser Xaa Asp
 1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: Nle
<221> NAME/KEY: MOD_RES
<222> LOCATION: (5)
<223> OTHER INFORMATION: Tyr(NO2)

<400> SEQUENCE: 5

Val Ala Xaa Ser Xaa
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: Nle
<221> NAME/KEY: MOD_RES
<222> LOCATION: (4)
<223> OTHER INFORMATION: Tyr(NO2)

<400> SEQUENCE: 6

Ala Xaa Ser Xaa Asp

```
   1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: Nle
<221> NAME/KEY: MOD_RES
<222> LOCATION: (5)
<223> OTHER INFORMATION: Tyr(NO2)

<400> SEQUENCE: 7

Val Ala Xaa Ser Xaa
  1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (4)
<223> OTHER INFORMATION: Nle
<221> NAME/KEY: MOD_RES
<222> LOCATION: (6)
<223> OTHER INFORMATION: Tyr(NO2)

<400> SEQUENCE: 8

Xaa Val Ala Xaa Ser Xaa
  1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (4)
<223> OTHER INFORMATION: Nle

<400> SEQUENCE: 9

Xaa Val Ala Xaa Ser
  1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (4)
<223> OTHER INFORMATION: Nle
```

```
<400> SEQUENCE: 10

Xaa Val Ala Xaa Ser Phe Asp
 1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (4)
<223> OTHER INFORMATION: Nle

<400> SEQUENCE: 11

Xaa Val Ala Xaa Ser Tyr Asp
 1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (4)
<223> OTHER INFORMATION: Nle

<400> SEQUENCE: 12

Xaa Val Ala Xaa Ser Ala Asp
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (4)
<223> OTHER INFORMATION: Nle

<400> SEQUENCE: 13

Xaa Val Ala Xaa Ser Lys Asp
 1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (4)
```

```
<223> OTHER INFORMATION: Nle
<221> NAME/KEY: MOD_RES
<222> LOCATION: (6)
<223> OTHER INFORMATION: eAHA

<400> SEQUENCE: 14

Xaa Val Ala Xaa Ser Xaa Asp
 1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (3)
<223> OTHER INFORMATION: Nle
<221> NAME/KEY: MOD_RES
<222> LOCATION: (5)
<223> OTHER INFORMATION: Tyr(NO2)

<400> SEQUENCE: 15

Xaa Ala Xaa Ser Xaa Asp
 1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: Nle
<221> NAME/KEY: MOD_RES
<222> LOCATION: (4)
<223> OTHER INFORMATION: Tyr(NO2)

<400> SEQUENCE: 16

Xaa Xaa Ser Xaa Asp
 1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: Nle
<221> NAME/KEY: MOD_RES
<222> LOCATION: (5)
<223> OTHER INFORMATION: Tyr(NO2)

<400> SEQUENCE: 17

Val Ala Xaa Ser Xaa
 1               5

<210> SEQ ID NO 18
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: Nle
<221> NAME/KEY: MOD_RES
<222> LOCATION: (5)
<223> OTHER INFORMATION: Tyr(NO2)

<400> SEQUENCE: 18

Val Ala Xaa Ser Xaa
 1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: Nle
<221> NAME/KEY: MOD_RES
<222> LOCATION: (5)
<223> OTHER INFORMATION: Tyr(NO2)

<400> SEQUENCE: 19

Val Ala Xaa Ser Xaa
 1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: Nle
<221> NAME/KEY: MOD_RES
<222> LOCATION: (5)
<223> OTHER INFORMATION: Tyr(NO2)

<400> SEQUENCE: 20

Val Ala Xaa Ser Xaa
 1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: Nle
<221> NAME/KEY: MOD_RES
<222> LOCATION: (5)
<223> OTHER INFORMATION: Tyr(NO2)

<400> SEQUENCE: 21

Val Ala Xaa Ser Xaa
 1               5

<210> SEQ ID NO 22
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: Nle
<221> NAME/KEY: MOD_RES
<222> LOCATION: (5)
<223> OTHER INFORMATION: Tyr(NO2)

<400> SEQUENCE: 22

Val Ala Xaa Ser Xaa
 1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (6)
<223> OTHER INFORMATION: Tyr(NO2)

<400> SEQUENCE: 23

Xaa Val Ala Lys Ser Xaa Asp
 1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (6)
<223> OTHER INFORMATION: Tyr(NO2)

<400> SEQUENCE: 24

Xaa Val Ala Gln Ser Xaa Asp
 1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (6)
<223> OTHER INFORMATION: Tyr(NO2)

<400> SEQUENCE: 25

Xaa Val Ala Thr Ser Xaa Asp
 1               5
```

```
<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 26

Xaa Val Ala Xaa Ser Xaa Asp
  1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (4)
<223> OTHER INFORMATION: Cha
<221> NAME/KEY: MOD_RES
<222> LOCATION: (6)
<223> OTHER INFORMATION: Tyr(NO2)

<400> SEQUENCE: 27

Xaa Val Ala Xaa Ser Xaa Asp
  1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (6)
<223> OTHER INFORMATION: Tyr(NO2)

<400> SEQUENCE: 28

Xaa Val Ala His Ser Xaa Asp
  1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (4)
<223> OTHER INFORMATION: ACH
```

```
<221> NAME/KEY: MOD_RES
<222> LOCATION: (6)
<223> OTHER INFORMATION: Tyr(NO2)

<400> SEQUENCE: 29

Xaa Val Ala Xaa Ser Xaa Asp
 1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (4)
<223> OTHER INFORMATION: DNle
<221> NAME/KEY: MOD_RES
<222> LOCATION: (6)
<223> OTHER INFORMATION: Tyr(NO2)

<400> SEQUENCE: 30

Xaa Val Ala Xaa Ser Xaa Asp
 1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (4)
<223> OTHER INFORMATION: 3pyr
<221> NAME/KEY: MOD_RES
<222> LOCATION: (6)
<223> OTHER INFORMATION: Tyr(NO2)

<400> SEQUENCE: 31

Xaa Val Ala Xaa Ser Xaa Asp
 1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (4)
<223> OTHER INFORMATION: Hyp
<221> NAME/KEY: MOD_RES
<222> LOCATION: (6)
<223> OTHER INFORMATION: Tyr(NO2)

<400> SEQUENCE: 32

Xaa Val Ala Xaa Ser Xaa Asp
 1               5
```

```
<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (4)
<223> OTHER INFORMATION: ACP
<221> NAME/KEY: MOD_RES
<222> LOCATION: (6)
<223> OTHER INFORMATION: Tyr(NO2)

<400> SEQUENCE: 33

Xaa Val Ala Xaa Ser Xaa Asp
 1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 34

Xaa Val Lys Xaa Ser Xaa Asp
 1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (3)
<223> OTHER INFORMATION: DAla
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 35

Xaa Val Xaa Xaa Ser Xaa Asp
 1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<221> NAME/KEY: MOD_RES
<222> LOCATION: (1)
<223> OTHER INFORMATION: Abz
<221> NAME/KEY: MOD_RES
<222> LOCATION: (3)
<223> OTHER INFORMATION: Tic
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 36

Xaa Val Xaa Xaa Ser Xaa Asp
 1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (3)
<223> OTHER INFORMATION: ACH
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 37

Xaa Val Xaa Xaa Ser Xaa Asp
 1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (3)
<223> OTHER INFORMATION: Met(O)
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 38

Xaa Val Xaa Xaa Ser Xaa Asp
 1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
```

```
<222> LOCATION: (1)
<223> OTHER INFORMATION: Abz
<221> NAME/KEY: MOD_RES
<222> LOCATION: (3)
<223> OTHER INFORMATION: 2Nal
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 39

Xaa Val Xaa Xaa Ser Xaa Asp
 1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (3)
<223> OTHER INFORMATION: ACP
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 40

Xaa Val Xaa Xaa Ser Xaa Asp
 1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (3)
<223> OTHER INFORMATION: DLys
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 41

Xaa Val Xaa Xaa Ser Xaa Asp
 1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
```

```
<223> OTHER INFORMATION: Abz
<221> NAME/KEY: MOD_RES
<222> LOCATION: (3)
<223> OTHER INFORMATION: DGln
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 42

Xaa Val Xaa Xaa Ser Xaa Asp
  1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (3)
<223> OTHER INFORMATION: 3pyr
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 43

Xaa Val Xaa Xaa Ser Xaa Asp
  1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (3)
<223> OTHER INFORMATION: Cha
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 44

Xaa Val Xaa Xaa Ser Xaa Asp
  1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
```

```
<221> NAME/KEY: MOD_RES
<222> LOCATION: (2)
<223> OTHER INFORMATION: DVal
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 45

Xaa Xaa Ala Xaa Ser Xaa Asp
 1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 46

Xaa Gln Ala Xaa Ser Xaa Asp
 1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 47

Xaa Lys Ala Xaa Ser Xaa Asp
 1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: Tic
<221> NAME/KEY: MOD_RES
<222> LOCATION: (4)
<223> OTHER INFORMATION: hLeu
<221> NAME/KEY: MOD_RES
```

```
<222> LOCATION: (6)
<223> OTHER INFORMATION: Tyr(NO2)

<400> SEQUENCE: 48

Xaa Xaa Ala Xaa Ser Xaa Asp
 1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: ACH
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 49

Xaa Xaa Ala Xaa Ser Xaa Asp
 1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: Met(O)
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 50

Xaa Xaa Ala Xaa Ser Xaa Asp
 1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: 3pyr
<221> NAME/KEY: MOD_RES
<222> LOCATION: (4)
<223> OTHER INFORMATION: hLeu
<221> NAME/KEY: MOD_RES
<222> LOCATION: (6)
```

<223> OTHER INFORMATION: Tyr(NO2)

<400> SEQUENCE: 51

Xaa Xaa Ala Xaa Ser Xaa Asp
 1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: 2Nal
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 52

Xaa Xaa Ala Xaa Ser Xaa Asp
 1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 53

Xaa Leu Ala Xaa Ser Xaa Asp
 1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: Cha
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 54

```
Xaa Xaa Ala Xaa Ser Xaa Asp
 1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: Bip
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 55

Xaa Xaa Ala Xaa Ser Xaa Asp
 1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: Bip
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 56

Xaa Xaa Ala Xaa Tyr Xaa Asp
 1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: Bip
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 57

Xaa Xaa Ala Xaa Leu Xaa Asp
```

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: Bip
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 58

Xaa Xaa Ala Xaa Lys Xaa Asp
 1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: Bip
<221> NAME/KEY: MOD_RES
<222> LOCATION: (4)
<223> OTHER INFORMATION: hLeu
<221> NAME/KEY: MOD_RES
<222> LOCATION: (6)
<223> OTHER INFORMATION: Tyr(NO2)

<400> SEQUENCE: 59

Xaa Xaa Ala Xaa Asp Xaa Asp
 1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: Bip
<221> NAME/KEY: MOD_RES
<222> LOCATION: (4)
<223> OTHER INFORMATION: hLeu
<221> NAME/KEY: MOD_RES
<222> LOCATION: (5)
<223> OTHER INFORMATION: Abu
<221> NAME/KEY: MOD_RES
<222> LOCATION: (6)
<223> OTHER INFORMATION: Tyr(NO2)

<400> SEQUENCE: 60

Xaa Xaa Ala Xaa Xaa Xaa Asp
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: Bip
<221> NAME/KEY: MOD_RES
<222> LOCATION: (4)
<223> OTHER INFORMATION: hLeu
<221> NAME/KEY: MOD_RES
<222> LOCATION: (5)
<223> OTHER INFORMATION: Cha
<221> NAME/KEY: MOD_RES
<222> LOCATION: (6)
<223> OTHER INFORMATION: Tyr(NO2)

<400> SEQUENCE: 61

Xaa Xaa Ala Xaa Xaa Xaa Asp
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: Bip
<221> NAME/KEY: MOD_RES
<222> LOCATION: (4)
<223> OTHER INFORMATION: hLeu
<221> NAME/KEY: MOD_RES
<222> LOCATION: (5)
<223> OTHER INFORMATION: Met(O)
<221> NAME/KEY: MOD_RES
<222> LOCATION: (6)
<223> OTHER INFORMATION: Tyr(NO2)

<400> SEQUENCE: 62

Xaa Xaa Ala Xaa Xaa Xaa Asp
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: Bip
<221> NAME/KEY: MOD_RES
<222> LOCATION: (4)
<223> OTHER INFORMATION: hLeu

```
<221> NAME/KEY: MOD_RES
<222> LOCATION: (6)
<223> OTHER INFORMATION: Tyr(NO2)

<400> SEQUENCE: 63

Xaa Xaa Ala Xaa Thr Xaa Asp
 1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: Bip
<221> NAME/KEY: MOD_RES
<222> LOCATION: (4)
<223> OTHER INFORMATION: hLeu
<221> NAME/KEY: MOD_RES
<222> LOCATION: (5)
<223> OTHER INFORMATION: 3pyr
<221> NAME/KEY: MOD_RES
<222> LOCATION: (6)
<223> OTHER INFORMATION: Tyr(NO2)

<400> SEQUENCE: 64

Xaa Xaa Ala Xaa Xaa Xaa Asp
 1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: Bip
<221> NAME/KEY: MOD_RES
<222> LOCATION: (4)
<223> OTHER INFORMATION: hLeu
<221> NAME/KEY: MOD_RES
<222> LOCATION: (5)
<223> OTHER INFORMATION: BuGly
<221> NAME/KEY: MOD_RES
<222> LOCATION: (6)
<223> OTHER INFORMATION: Tyr(NO2)

<400> SEQUENCE: 65

Xaa Xaa Ala Xaa Xaa Xaa Asp
 1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
```

```
<222> LOCATION: (2)
<223> OTHER INFORMATION: Bip
<221> NAME/KEY: MOD_RES
<222> LOCATION: (4)
<223> OTHER INFORMATION: hLeu
<221> NAME/KEY: MOD_RES
<222> LOCATION: (5)
<223> OTHER INFORMATION: Hyp
<221> NAME/KEY: MOD_RES
<222> LOCATION: (6)
<223> OTHER INFORMATION: Tyr(NO2)

<400> SEQUENCE: 66

Xaa Xaa Ala Xaa Xaa Xaa Asp
 1               5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (5)
<223> OTHER INFORMATION: Nle
<221> NAME/KEY: MOD_RES
<222> LOCATION: (7)
<223> OTHER INFORMATION: Tyr(NO2)

<400> SEQUENCE: 67

Xaa Phe Val Ala Xaa Ser Xaa Asp
 1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: 3.Pyr
<221> NAME/KEY: MOD_RES
<222> LOCATION: (5)
<223> OTHER INFORMATION: Nle
<221> NAME/KEY: MOD_RES
<222> LOCATION: (7)
<223> OTHER INFORMATION: Tyr(NO2)

<400> SEQUENCE: 68

Xaa Xaa Val Ala Xaa Ser Xaa Asp
 1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
```

```
<223> OTHER INFORMATION: 1.Naph
<221> NAME/KEY: MOD_RES
<222> LOCATION: (5)
<223> OTHER INFORMATION: Nle
<221> NAME/KEY: MOD_RES
<222> LOCATION: (7)
<223> OTHER INFORMATION: Tyr(NO2)

<400> SEQUENCE: 69

Xaa Xaa Val Ala Xaa Ser Xaa Asp
 1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: 2.Naph
<221> NAME/KEY: MOD_RES
<222> LOCATION: (5)
<223> OTHER INFORMATION: Nle
<221> NAME/KEY: MOD_RES
<222> LOCATION: (7)
<223> OTHER INFORMATION: Tyr(NO2)

<400> SEQUENCE: 70

Xaa Xaa Val Ala Xaa Ser Xaa Asp
 1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (5)
<223> OTHER INFORMATION: Nle
<221> NAME/KEY: MOD_RES
<222> LOCATION: (7)
<223> OTHER INFORMATION: Tyr(NO2)

<400> SEQUENCE: 71

Xaa Tyr Val Ala Xaa Ser Xaa Asp
 1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: Bip
<221> NAME/KEY: MOD_RES
<222> LOCATION: (5)
<223> OTHER INFORMATION: Nle
```

```
<221> NAME/KEY: MOD_RES
<222> LOCATION: (7)
<223> OTHER INFORMATION: Tyr(NO2)

<400> SEQUENCE: 72

Xaa Xaa Val Ala Xaa Ser Xaa Asp
 1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (5)
<223> OTHER INFORMATION: Nle
<221> NAME/KEY: MOD_RES
<222> LOCATION: (7)
<223> OTHER INFORMATION: Tyr(NO2)

<400> SEQUENCE: 73

Xaa Lys Val Ala Xaa Ser Xaa Asp
 1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (5)
<223> OTHER INFORMATION: Nle
<221> NAME/KEY: MOD_RES
<222> LOCATION: (7)
<223> OTHER INFORMATION: Tyr(NO2)

<400> SEQUENCE: 74

Xaa Glu Val Ala Xaa Ser Xaa Asp
 1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (5)
<223> OTHER INFORMATION: Nle
<221> NAME/KEY: MOD_RES
<222> LOCATION: (7)
<223> OTHER INFORMATION: Tyr(NO2)

<400> SEQUENCE: 75

Xaa Leu Val Ala Xaa Ser Xaa Asp
 1               5
```

```
<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: Hyp
<221> NAME/KEY: MOD_RES
<222> LOCATION: (5)
<223> OTHER INFORMATION: Nle
<221> NAME/KEY: MOD_RES
<222> LOCATION: (7)
<223> OTHER INFORMATION: Tyr(NO2)

<400> SEQUENCE: 76

Xaa Xaa Val Ala Xaa Ser Xaa Asp
  1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (4)
<223> OTHER INFORMATION: (NMe)Nle
<221> NAME/KEY: MOD_RES
<222> LOCATION: (6)
<223> OTHER INFORMATION: Tyr(NO2)

<400> SEQUENCE: 77

Xaa Val Ala Xaa Ser Xaa Asp
  1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (3)
<223> OTHER INFORMATION: (NMe)Ala
<221> NAME/KEY: MOD_RES
<222> LOCATION: (4)
<223> OTHER INFORMATION: Nle
<221> NAME/KEY: MOD_RES
<222> LOCATION: (6)
<223> OTHER INFORMATION: Tyr(NO2)

<400> SEQUENCE: 78

Xaa Val Xaa Xaa Ser Xaa Asp
  1               5

<210> SEQ ID NO 79
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (4)
<223> OTHER INFORMATION: Aib
<221> NAME/KEY: MOD_RES
<222> LOCATION: (6)
<223> OTHER INFORMATION: Tyr(NO2)

<400> SEQUENCE: 79

Xaa Val Ala Xaa Ser Xaa Asp
  1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (3)
<223> OTHER INFORMATION: Aib
<221> NAME/KEY: MOD_RES
<222> LOCATION: (4)
<223> OTHER INFORMATION: Nle
<221> NAME/KEY: MOD_RES
<222> LOCATION: (6)
<223> OTHER INFORMATION: Tyr(NO2)

<400> SEQUENCE: 80

Xaa Val Xaa Xaa Ser Xaa Asp
  1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: Deg
<221> NAME/KEY: MOD_RES
<222> LOCATION: (4)
<223> OTHER INFORMATION: Nle
<221> NAME/KEY: MOD_RES
<222> LOCATION: (6)
<223> OTHER INFORMATION: Tyr(NO2)

<400> SEQUENCE: 81

Xaa Xaa Ala Xaa Ser Xaa Asp
  1               5

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
```

```
<222> LOCATION: (1)
<223> OTHER INFORMATION: nBu
<221> NAME/KEY: MOD_RES
<222> LOCATION: (2)
<223> OTHER INFORMATION: D.Ser
<221> NAME/KEY: MOD_RES
<222> LOCATION: (3)
<223> OTHER INFORMATION: D.Nle
<221> NAME/KEY: MOD_RES
<222> LOCATION: (4)
<223> OTHER INFORMATION: D.Ala
<221> NAME/KEY: MOD_RES
<222> LOCATION: (5)
<223> OTHER INFORMATION: D.Val
<221> NAME/KEY: MOD_RES
<222> LOCATION: (6)
<223> OTHER INFORMATION: p.Aba

<400> SEQUENCE: 82

Xaa Xaa Xaa Xaa Xaa Xaa
 1               5

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Bz
<221> NAME/KEY: MOD_RES
<222> LOCATION: (4)
<223> OTHER INFORMATION: Statine
<221> NAME/KEY: MOD_RES
<222> LOCATION: (6)
<223> OTHER INFORMATION: eAha

<400> SEQUENCE: 83

Xaa Val Ala Xaa Ser Xaa
 1               5

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: p.Aba
<221> NAME/KEY: MOD_RES
<222> LOCATION: (3)
<223> OTHER INFORMATION: Nle
<221> NAME/KEY: MOD_RES
<222> LOCATION: (5)
<223> OTHER INFORMATION: Tyr(NO2)

<400> SEQUENCE: 84

Xaa Xaa Xaa Ser Xaa Asp
 1               5

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
                            peptide
<221> NAME/KEY: MOD_RES
<222> LOCATION: (1)
<223> OTHER INFORMATION: Abz
<221> NAME/KEY: MOD_RES
<222> LOCATION: (2)
<223> OTHER INFORMATION: Cmpi
<221> NAME/KEY: MOD_RES
<222> LOCATION: (3)
<223> OTHER INFORMATION: Nle
<221> NAME/KEY: MOD_RES
<222> LOCATION: (5)
<223> OTHER INFORMATION: Tyr(NO2)

<400> SEQUENCE: 85

Xaa Xaa Xaa Ser Xaa Asp
  1               5

<210> SEQ ID NO 86
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: N-Benzoyl
<221> NAME/KEY: MOD_RES
<222> LOCATION: (4)
<223> OTHER INFORMATION: L-norleucine

<400> SEQUENCE: 86

Xaa Val Ala Xaa
  1

<210> SEQ ID NO 87
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: N-Benzoyl
<221> NAME/KEY: MOD_RES
<222> LOCATION: (4)
<223> OTHER INFORMATION: L-norleucine bromomethyl ketone

<400> SEQUENCE: 87

Xaa Val Ala Xaa
  1

<210> SEQ ID NO 88
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: N-Benzoyl
<221> NAME/KEY: MOD_RES
<222> LOCATION: (4)
<223> OTHER INFORMATION: L-norleucine 2, 6-bis (trifluoromethyl)
      benzoyloxymethyl ketone

<400> SEQUENCE: 88

Xaa Val Ala Xaa
  1
```

```
<210> SEQ ID NO 89
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: N-Benzoyl
<221> NAME/KEY: MOD_RES
<222> LOCATION: (4)
<223> OTHER INFORMATION: L-norleucine 2, 6-dimethylbenzoyloxymethyl
      ketone

<400> SEQUENCE: 89

Xaa Val Ala Xaa
 1

<210> SEQ ID NO 90
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: N-Benzoyl
<221> NAME/KEY: MOD_RES
<222> LOCATION: (4)
<223> OTHER INFORMATION: L-norleucine 2-hydroxybenzoyloxymethyl ketone

<400> SEQUENCE: 90

Xaa Val Ala Xaa
       1

<210> SEQ ID NO 91
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: N-Benzoyl
<221> NAME/KEY: MOD_RES
<222> LOCATION: (4)
<223> OTHER INFORMATION: L-norleucine 2, 6-dichlorobenzoyloxymethyl
      ketone

<400> SEQUENCE: 91

Xaa Val Ala Xaa
 1

<210> SEQ ID NO 92
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: N-Benzoyl
<221> NAME/KEY: MOD_RES
<222> LOCATION: (4)
<223> OTHER INFORMATION: L-norleucine benzoyloxymethyl ketone

<400> SEQUENCE: 92
```

```
Xaa Val Ala Xaa
 1
```

<210> SEQ ID NO 93
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: N-Benzoyl
<221> NAME/KEY: MOD_RES
<222> LOCATION: (4)
<223> OTHER INFORMATION: L-norleucine 2, 3, 4, 5,
      6-pentafluorobenzoyloxymethyl ketone

<400> SEQUENCE: 93

```
Xaa Val Ala Xaa
 1
```

<210> SEQ ID NO 94
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: N-Benzoyl
<221> NAME/KEY: MOD_RES
<222> LOCATION: (4)
<223> OTHER INFORMATION: L-norleucine 1, 1-dimethylpropyloxymethyl
      ketone

<400> SEQUENCE: 94

```
Xaa Val Ala Xaa
 1
```

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: N-Benzoyl
<221> NAME/KEY: MOD_RES
<222> LOCATION: (4)
<223> OTHER INFORMATION: L-norleucine
<221> NAME/KEY: MOD_RES
<222> LOCATION: (5)
<223> OTHER INFORMATION: N(-benxyloxycarbonyl)-D-serinyl
      -(0-tert-butyl) oxymethyl ketone

<400> SEQUENCE: 95

```
Xaa Val Ala Xaa Xaa
 1               5
```

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES

```
<222> LOCATION: (1)
<223> OTHER INFORMATION: N-Benzoyl
<221> NAME/KEY: MOD_RES
<222> LOCATION: (4)
<223> OTHER INFORMATION: L-norleucine
<221> NAME/KEY: MOD_RES
<222> LOCATION: (5)
<223> OTHER INFORMATION: N(-benxyloxycarbonyl)-D-serineoxy
      methyl ketone

<400> SEQUENCE: 96

Xaa Val Ala Xaa Xaa
 1               5

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: N-Benzoyl
<221> NAME/KEY: MOD_RES
<222> LOCATION: (4)
<223> OTHER INFORMATION: L-norleucine
<221> NAME/KEY: MOD_RES
<222> LOCATION: (5)
<223> OTHER INFORMATION: 2-furanoxy methyl ketone

<400> SEQUENCE: 97

Xaa Val Ala Xaa Xaa
 1               5

<210> SEQ ID NO 98
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: N-Benzoyl
<221> NAME/KEY: MOD_RES
<222> LOCATION: (4)
<223> OTHER INFORMATION: L-norleucine 2, 6-dichlorophenylacyloxy
      methyl ketone

<400> SEQUENCE: 98

Xaa Val Ala Xaa
 1

<210> SEQ ID NO 99
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Ethyl-(S)-(E)-3-(tert-butoxy carbonyl)
<221> NAME/KEY: MOD_RES
<222> LOCATION: (4)
<223> OTHER INFORMATION: amino-6-methyl-hept-2-enoate

<400> SEQUENCE: 99

Xaa Val Ala Xaa
 1
```

<210> SEQ ID NO 100
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: (S)-(E)-3-(tert-butoxy carbonyl)
<221> NAME/KEY: MOD_RES
<222> LOCATION: (4)
<223> OTHER INFORMATION: amino-6-methyl-hept-2-enoic acid

<400> SEQUENCE: 100

Xaa Val Ala Xaa
 1

<210> SEQ ID NO 101
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: 1,1,1-Trifluoroethyl-(S)-(E)-3-(tert-butoxy
      carbonyl)
<221> NAME/KEY: MOD_RES
<222> LOCATION: (4)
<223> OTHER INFORMATION: amino-6-methyl-hept-2-enoate

<400> SEQUENCE: 101

Xaa Val Ala Xaa
 1

<210> SEQ ID NO 102
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Ethyl-(S)-(E)-3-(N-benzoyl)
<221> NAME/KEY: MOD_RES
<222> LOCATION: (4)
<223> OTHER INFORMATION: amino-6-methyl-hept-2-enoate

<400> SEQUENCE: 102

Xaa Val Ala Xaa
 1

<210> SEQ ID NO 103
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: (S)-(E)-3-(tert-butoxycarbonylamino)
<221> NAME/KEY: MOD_RES
<222> LOCATION: (4)
<223> OTHER INFORMATION: amino-1-phenylsulfonyl-5-methyl-1-hexene

<400> SEQUENCE: 103

Xaa Val Ala Xaa

-continued

```
<210> SEQ ID NO 104
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: (S)-(E)-3-(tert-butoxycarbonylamino)
<221> NAME/KEY: MOD_RES
<222> LOCATION: (4)
<223> OTHER INFORMATION: amino-1-methylsulfonyl-5-methyl-1-hexene

<400> SEQUENCE: 104

Xaa Val Ala Xaa
  1

<210> SEQ ID NO 105
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Diethyl(S)-(E)-3-(tert-butoxycarbonylamino)
<221> NAME/KEY: MOD_RES
<222> LOCATION: (4)
<223> OTHER INFORMATION: amino-5-methylhexenylsulfonate

<400> SEQUENCE: 105

Xaa Val Ala Xaa
  1
```

SUBSTRATES AND INHIBITORS OF PROTEOLYTIC ENZYMES

The present invention relates to the field of compounds which are substrates or inhibitors of proteolytic enzymes and to apparatus and methods for identifying substrates or inhibitors for proteolytic enzymes.

Many therapeutically useful drugs act as enzyme inhibitors. In particular, proteolytic enzyme inhibitors have been the focus of much attention in the pharmaceutical industry, because they play a variety of roles in a multitude of biological systems. Their proteolytic activities are related to processes ranging from cell invasion associated with metastatic cancer to evasion of an immune response, as seen in certain parasitic organisms; from nutrition to intracellular signalling to the site-specific proteolysis of viral proteases and eukaryotic hormone-processing enzymes. However, the traditional random screening methods for the identification of lead molecules as inhibitors of proteolytic enzymes are often laborious and time-consuming. Therefore new and efficient methods which can accelerate the drug discovery process are greatly in demand.

We consider that proteases contain an active catalytic site which tends to become increasingly activated as the recognition pockets[1] ($S_1$ and $S_2$ etc) and ($S_1'$ and $S_2'$ etc) become better occupied. Therefore, it is important that those parts ($P_1$ and $P_2$ etc) ($P_1'$ and $P_2'$ etc) of the inhibitor that best fit into these pockets are identified as quickly as possible in order to design novel protease inhibitors. Therefore, we have devised a combinatorial method for the rapid identification of these binding motifs which will greatly expedite the synthesis of inhibitors of a variety of proteolytic enzymes such as aspartyl proteases, serine proteases, metallo proteases and cysteinyl proteases.

Proteases of interest include (but are not limited to):

1. Aspartyl proteases, such as renin, HIV, cathepsin D and cathespin E etc.
2. Metalloproteases, such as ECE, gelatinase A and B, collagenases, stromolysins etc.
3. Cysteinyl proteases, such as apopain, ICI, DerPI, cathepsin B, cathepsin K etc.
4. Serine proteases, such as thrombin, factor VIIa, factor Xa, elastase, trypsin.
5. Threonyl proteases, such as proteasome S.

The use of a fluorescence resonance energy transfer (FRET) substrate for the analysis of proteolytic enzyme specificity was first published by Carmel.[2] Since then many different quenched fluorogenic substrates for measuring enzyme inhibition have been described in the literature.[4-11] These substrates contain a fluorophore, F, in a P position (vide supra), which is quenched by another group, Q, present in a P' position (vide supra) and separated from F by the scissile bond. The advantage of the positioning of these residues, F and Q, is that cleavage of a peptide bond occurs between the two natural residues and, therefore, represents a more natural hydrolytic event rather than the cleavage and release of a C-terminal chromophore.

For example, Bratovanova and Petkov[12] have synthesised fluorogenic substrates from peptide 4-nitroanilides. N-acylation of peptide 4-nitroanilides with the aminobenzoyl (ABz) group yielded substrates that are internally quenched by the presence of the 4-nitroanilide moiety. Upon hydrolysis of the aminoacyl-4-nitroanilide bond, the highly fluorescent N-ABz group is released attached either to an amino acid or peptide.

Immobilised libraries; where substrates are attached to a polymer or biopolymer support, have also been used for mapping protease binding sites.[13] Singh et al. reported recently that enzymatic substrate activity of 38 selected octapeptides attached via a linker to controlled pore glass is predictive of the same activity of similar peptides in solution. However, these results are preliminary and only for a specific example. Therefore, it is not clear whether immobilised substrates attached to polymers can reliably replace soluble substrates in mapping the hindered protease binding sites, especially since the hydrophilic or lipophilic nature of the polymer and the size of the interstices within the polymer are bound to influence the reaction between the enzyme and its substrates.

Mixtures of internally quenched, fluorogenic substrates have also recently been described in which the quencher group, Q, is 2,4-dinitrophenyl (Dnp) and is attached to the P side of the scissile bond, while the fluorogenic group, is N-methyl anthranilic acid (Nma) and is attached to the P' side.[14]

Examples of other Donor-Acceptor Chromophore Pairs that have been applied to Biological Systems are shown in Table 1.

TABLE 1

Donor-Acceptor Chromophore Pairs That Have Been Applied To Biological Samples

| Donor | Acceptor | Donor | Acceptor |
| --- | --- | --- | --- |
| Naphthalene | Dansyl | IAEDANS | TNP-ATP |
| IANBD | DDPM | ε-A | IANBD |
| IAEDANS | DDPM | NBD | SRH |
| DNSM | LY | ISA | TNP |
| IAEDANS | IANBD | Dansyl | ODR |
| E-A | F$_2$DNB | DANZ | IAF |
| Pyrene | Bimane | FNAI | EITC |
| ANAI | IPM | NBD | LRH |
| IAANS | IAF | IAF | EIA |
| ε-A | F$_2$DPS | FITC | ENAI |
| ε-A | DDPM | Proflavin | ETSC |
| IAEDANS | TNP | CPM | TNP-ATP |
| MNA | DACM | IAEDANS | IAF |
| PM | NBD | CPM | Fluorescein |
| FITC | TNP-ATP | IAEDANS | FITC |
| DANZ | DABM | FITC | TMR |
| NCP | CPM | IAF | TMR |
| NAA | DNP | CF | TR |
| LY | TNP-ATP | CPM | FTS |
| IAF | diI-C$_{18}$ | ε-A | TNP-ATP |
| IAF | TMR | CPM | FM |
| FMA | FMA | LY | EM |
| PM | DMAMS | FITC | EITC |
| mBBR | FITC | IAEDANS | DiO-C$_{14}$ |
| mBBR | DABM | IAF | ErITC |
| ε-A | NBD | FITC | EM |
| Pyrene | Coumarin | FITC | ETSC |

TABLE 1-continued

Donor-Acceptor Chromophore Pairs That Have Been Applied To Biological Samples

| Donor | Acceptor | Donor | Acceptor |
|-------|----------|-------|----------|
| IPM   | FNAI     | FITC  | ErITC    |
| IAEDANS | DABM   | BPE   | CYS      |

ANAI, 2-anthracene N-acetylimidazole; BPE, B-phycoerythrin; CF, carboxyfluorescein succinimidyl ester; CPM, 7-doethylamino-3-(4'maleimidylphenyl)-4-methylcoumarin; CY5, carboxymethylindocyanine-N-hydroxysuccinimidyl ester; diI-$C_{18}$, 1,1'-dioctadecyl-3,3,3',3'-tetramethyl-indocarbocyanine; DiO-$C_{14}$, 3,3'-ditetradecyloxacarbocyanine; DABM, 4-dimethylaniniphenylazo-phenyl-4'-maleimide; DACM, (7-(dimethylamino)coumarin-4-yl)-acetyl; DANZ, dansylaziridine; DDPM, N-(4-dimethylamino-3-5-dinitrophenyl)maleimide; DACM, di-methylamino-4-maleimidostilbene; DMSM, N-(2,5-dimethoxystiben-4-yl)-maleimide; DNP, 2,4-dinitrophenyl; ε-A, 1,$N^6$-ethenoadenosine; EIA, 5-(iodoacetetamido)eosin; EITC, eosin-5-isothiocyanate; ENAI, eosin N-acetylimidazole; EM, eosin maleimide; ErITC, erythrosin-5'-isothiocyanate; ETSC, eosin thiosemicarbazide; $F_2$DPB, 1,5-difluoro-2,4'-dinitrobenzene; $F_2$DPS, 4,4'-difluro-3,3'dinitropheylsulphone; FITC, fluorescein N-acetylimidazole; FTS, fluorescein thiosemicarbazide; IAANS; 2-((4'-iodoacetamido)anilino)naphthalene-6-sulphonic acid; IAEDANS, 5-(2-((iodoacetyl)amino)ethylamino)-naphthlene-1-sulphonic acid; IAF, 5-iodoacetamidofluorescein; IANBD, N-((2-(iodoacetoxy)ethyl)-N-methyl)amino-7-nitrobenz-2-oxa1,3,diazole; IPM, 3(4-isothiocyanatophenyl)7-diethyl-4-methylcoumarin; ISA, 4-(iodoacetamido)salicylic acid; LRH, lissaminerho-2,1,3-benzoxadiazol-4-yl; NCP, N-cyclohexyl-N'-(1-pyrenyl)carbodiimide; ODR, octadecylrhodamine; PM, N-(l-pyrene)-maleimide; SRH sulphurhodamine; TMR, teramethylrhodamine; TNP, trinitrophenyl; TR, Texas red.

from: Wu, P. and Brand, L. 1994. Anal. Biochem. 218, 1–13.

The specificity of soluble peptide libraries have been determined.[15,16] Berman et al. described[16] an HPLC mass spectrometry technique in which 6 mixtures of 128 peptides were synthesised which were N-terminally labelled with the Dnp group in order to allow UV monitoring on the HPLC. The disadvantage of this approach is that each assay mixture has to be individually analysed, because no fluorogenic substrate is revealed, and that the effective concentration of each separate component is limited by the size of the mixture because of overall solubility factors. Drevin et al.[17] have suggested the use of individually synthesised fluorogenic substrates for the determination of enzyme activity using a chromophore which chelates lanthanide ions. Garmann and Phillips have suggested the use of FRET substrates in which the fluorogenic and quencher moieties are attached via thiol or amino functional groups after the peptide has been synthesised, but this has the disadvantage that they are not in library form and that these functional amino and thiol groups need to be selectively revealed after the peptide has been synthesised. Wang et al. have suggested the use of the EDANS and DABCYL fluorescor and quencher pairing for the individual synthesis of substrates for proteolytic enzymes.

The above methods which have used FRET techniques for the mapping of the active site around a specific protease suffer from one or more of the following disadvantages:

i. because of general aqueous insolubility they do not produce mixtures of compounds in a form suitable for high throughput screening in aqueous solution.

ii. the derivatised compounds cannot be prepared in combinatorial library form using solid phase techniques.

iii. the mixtures which have been used[8,9] were not self-decoding, and needed time-consuming deconvolutive resynthesis for identification of the active molecules.

DESCRIPTION OF THE DRAWINGS

FIGS. 1 to 14 inclusive exemplify component distributions in the plates of a library matrix;

BRIEF DESCRIPTION OF THE INVENTION

Figure 15:
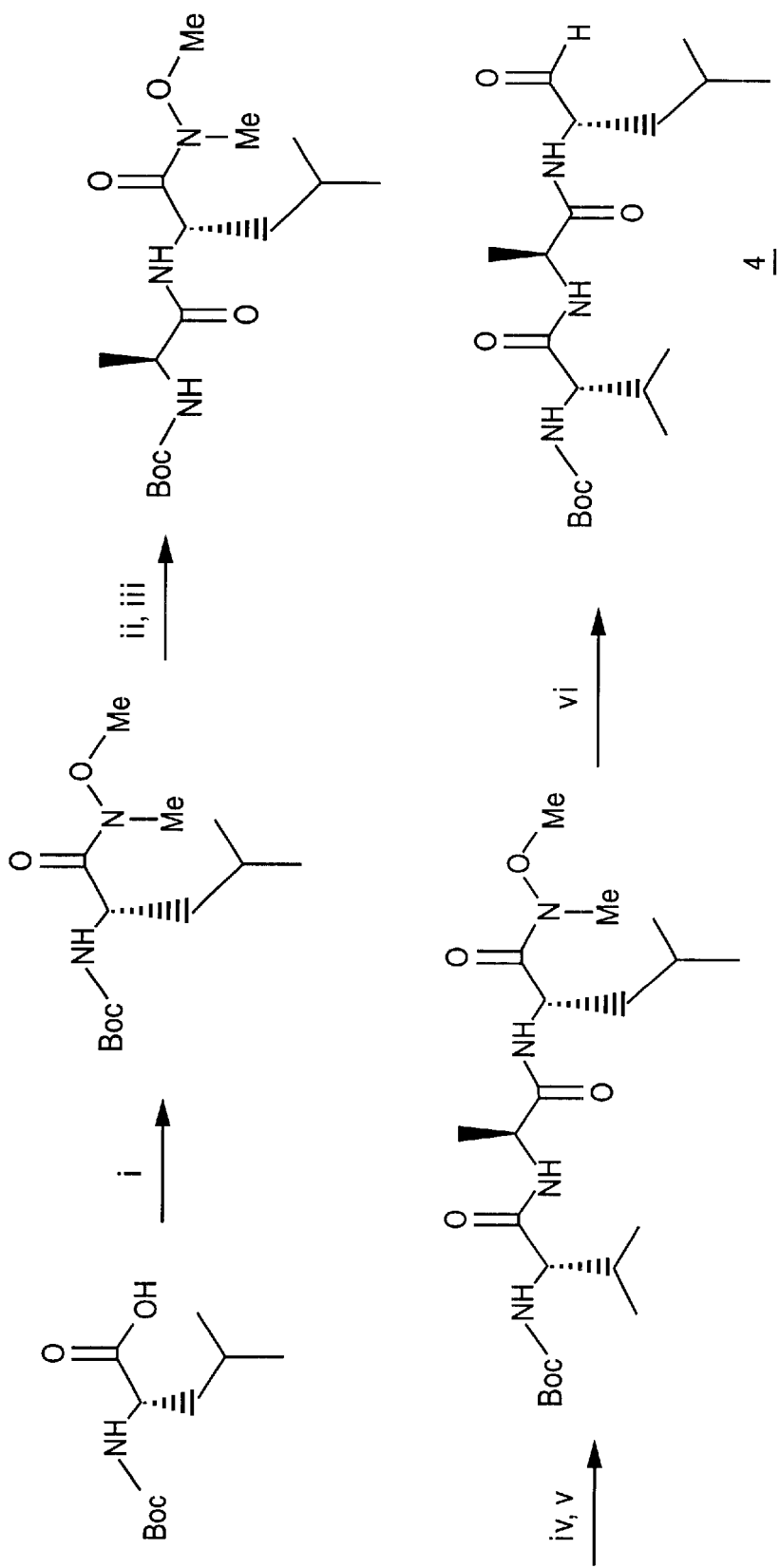
FIG. 15 illustrates a reaction scheme for production of compound number 4: Boc-Val-Ala-Leu-H wherein i. isobutylchloroformate, N-methylmorpholine, then N,O-dimethylhydroxylamine HCl, THF. ii. HCl, dioxan. iii. isobutylchloroformate, N-methylmorpholine, then Boc-Ala-OH, THF. iv. HCl, dioxan. V. Boc-Val-Osuc, N-methylmorpholine, DMF. Vi. LAH.

The present invention relates to the field of:

i. Compounds which are substrates or inhibitors of proteolytic enzymes.

ii. Apparatus and methods which provide the rapid generation of structure-activity relationships using auto-deconvoluting combinatorial libraries, which facilitate the invention of novel inhibitors of proteolytic enzymes.

iii. Apparatus and methods which provide the detection and measurement of proteolytic enzyme activity using combinatorial FRET (fluorescence resonance energy transfer) libraries of molecules.

iv. Apparatus and methods which provide the establishment of biological assays for proteolytic enzymes through the rapid discovery of highly active substrates for proteolytic enzymes.

We describe herein apparatus and methods which can be used for the rapid generation of structure-activity relationship (SAR) data and, therefore, the characterisation of the binding motif of any protease, and which will, therefore, facilitate:

i. the development of a sensitive enzyme inhibition assay by using the best compound in the library as the fluorogenic substrate for the proteolytic enzyme under scrutiny.

ii. the invention of novel compounds which are proteolytic enzyme inhibitors by rapid characterisation of the best binding motif.

iii. computer aided drug design to design potent inhibitors using known methodology, and also in prioritising which pre-synthesised compounds in the in-house and commercially available databases to assay.

In a first aspect the invention provides novel compounds represented by the formula A-B-C-D-nE-F [I] in which;

A represents a fluorescor internally quenched by F;

B, C, D, and E represent groups such that the scissile bond between any two of these groups is a suitable bond;

F represents a quencher capable of internally quenching the fluorescor A; and n represents an integer between 1 and 4 inclusive.

In some embodiments the suitable bond is an unsubstituted amide bond (see Example 1); in other embodiments the suitable bond is an ester bond (see Example 2).

In preferred embodiments B, C, D, E are amino acids or hydroxy acids. That is a molecule with an amine or hydroxy terminus and a carboxylic acid terminus. The amine/hydroxy group may be positioned on the same carbon atom or separated by a number of atoms and atom types.

The molecules may be cyclic or alicyclic. They may be linear or cyclic on the same structure

B-C-D-E or

or BCDE can be on a central scaffold (linear or cyclic)

 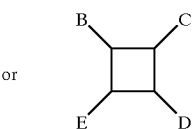

or one of the residues can be the backbone

Where the symbol -B-C-D-E- or -B-C-D-nE- is used herein, it is to be understood to include all of these linear and cyclic variants within its definition.

At least one but not all the bonds between B, C, D, E need to be scissile. Non scissile bonds may include sulphonamide, urea, aminomethylene.

Several non-limiting examples of "scaffold" molecules are shown in Table 2, in which substituents $R_1$–$R_4$ correspond to possible variable groups B, C, D and E.

In a second aspect the invention provides a combinatorial library of FRET compounds comprising a mixture of compounds of formula [I].

In a third aspect the invention provides for the use of such a combinatorial FRET library in a method which provides rapid generation of structure-activity relationships (SAR) which comprises detection and measurement of proteolytic enzyme activity by carrying out an assay with a library of combinatorial FRET (fluorescence resonance energy transfer) molecules to find a substrate or substrates for the enzyme. According to this method an identified substrate can be synthesised and used in biological assay for proteolytic enzymes. Novel substrates are included in the scope of the invention.

In a forth aspect the invention provides for the use of such a combinatorial FRET library in a method for detection and measurement of proteolytic enzyme activity against compounds of the library.

In a fifth aspect the invention provides a method which comprises the identification of an enzyme inhibitor or inhibitors wherein a FRET compound which has been

TABLE 2

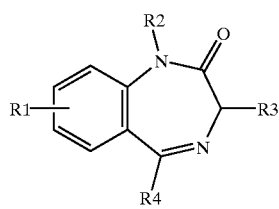

TABLE 2-continued

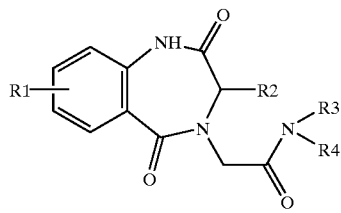

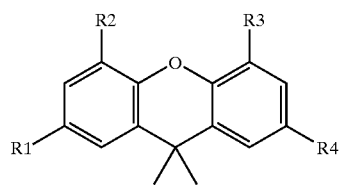

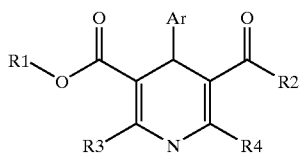

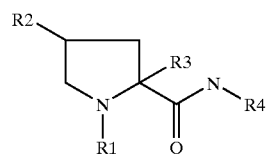

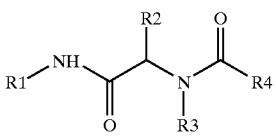

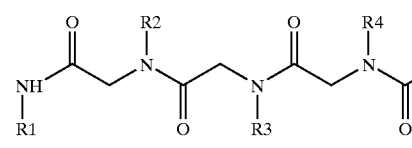

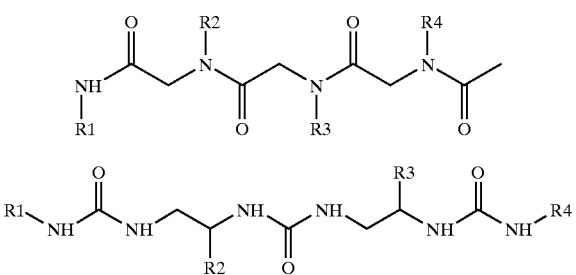

identified as a substrate is used in an inhibition assay with the enzyme separately against a panel of possible inhibitors.

In a sixth aspect the invention provides a set of compounds which comprises two complementary FRET compound libraries. Such a set will be referred to hereafter as "apparatus" because it allows for the screening or assay method for identifying substrates or inhibitors of proteolytic enzymes. This set of compounds constituting an apparatus is capable of providing an auto-deconvoluting combinatorial library as will be described below.

In a seventh aspect the invention provides a method of identifying and synthesising an inhibitor of a proteolytic enzyme which comprises detection and measurement of proteolytic enzyme activity by carrying out an assay with a library of combinatorial FRET (fluorescence resonance energy transfer) molecules, deconvoluting the library to find a substrate or substrates for the enzyme and synthesis of an inhibitor based on the substrate or substrates. The direct product of this method is one or more novel proteolytic enzyme inhibitors.

In an eighth aspect the invention provides an inhibition assay which uses a FRET molecule, which has been identified as a substrate for the enzyme, wherein the molecule is assayed with the enzyme separately against a panel of possible inhibitors.

In a ninth aspect the invention provides a complementary pair of compound libraries L1 and L2 which constitute a set containing compounds of formula:

$$A_a\text{-}B_b\text{-}C_c\text{-}D_d\text{-}n(E_e)\text{-}F_f\text{-}G_g$$

giving a×b×c×d×e×f×g=Mn compounds in each library, there being a predetermined number (P1, P2) of mixtures each consisting of a predetermined number (Q1, Q2) of individual identifiable compounds in each library, wherein both L1 and L2 contain the same Mn compounds, but wherein any two compounds which are found together in one mixture of Q1 compounds of L1 are not found together in any one of the P2 mixtures of L2.

In a tenth aspect the invention provides a method of screening for enzymic activity using the libraries L1, L2 described above in which the P1 mixtures of L1 and the P2 mixtures of L2 are each placed separately into individual wells of well plates, the well plates having wells arranged in a format adapted to allow deduction of a unique active compound formula from the presence of activity in one well of L1 and one well of L2.

The apparatus of the invention preferably comprises two complementary compound libraries, L1 and L2, each containing n×1600 compounds of the invention, of the type $A\text{-}B_{1\text{-}10}\text{-}C_{1\text{-}10}\text{-}D_{1\text{-}8}\text{-}n(E_{1\text{-}2})\text{-}F\text{-}G$ [II], in which:

A=a fluorescor internally quenched by F, preferably an unsubstituted or substituted anthranilic acid derivative, connected by an amide bond to B B, C, D, E, are natural or unnatural amino acid residues connected together by suitable bonds, although B, C, D and E can be any set of groups, provided that the scissile bond between D-E is an unsubstituted bond.

F=a quencher capable of internally quenching the fluorescor A, preferably an unsubstituted or substituted 3-nitrotyrosine derivative.

G=optionally present and is a hydrophilic moiety, preferably an aspartyl amide moiety. If present, G advantageously ensures that all compounds in the library are imparted with aqueous solubility. Also, G should not be a substrate for any type of enzyme.

n=any integer between 1 and 4 inclusive.

In an alternative, the scissile bond could be between B-C or C-D.

(Note that A and F herein correspond generally and respectively to moieties F and Q of the prior art referred to above).

The numbers represented in subscript following residues B, C, D and E refer to the number of possibilities from which those residues are selected. Thus, by way of illustrative example, $A\text{-}B_{1\text{-}5}\text{-}C\text{-}D\text{-}E_{1\text{-}2}\text{-}F\text{-}G$ represents a mixture of the following ten compounds:

$A\text{-}B_1\text{-}C\text{-}D\text{-}E_1\text{-}F\text{-}G$
$A\text{-}B_2\text{-}C\text{-}D\text{-}E_1\text{-}F\text{-}G$
$A\text{-}B_3\text{-}C\text{-}D\text{-}E_1\text{-}F\text{-}G$
$A\text{-}B_4\text{-}C\text{-}D\text{-}E_1\text{-}F\text{-}G$
$A\text{-}B_5\text{-}C\text{-}D\text{-}E_1\text{-}F\text{-}G$
$A\text{-}B_1\text{-}C\text{-}D\text{-}E_2\text{-}F\text{-}G$
$A\text{-}B_1\text{-}C\text{-}D\text{-}E_2\text{-}F\text{-}G$
$A\text{-}B_3\text{-}C\text{-}D\text{-}E_2\text{-}F\text{-}G$
$A\text{-}B_4\text{-}C\text{-}D\text{-}E_2\text{-}F\text{-}G$
$A\text{-}B_5\text{-}C\text{-}D\text{-}E_2\text{-}F\text{-}G$ The general combinatorial formula for each library can be expressed as:

$$A_1\text{-}B_{10}\text{-}C_{10}\text{-}D_8\text{-}n(E_2)\text{-}F_1\text{-}G_1 \qquad [III]$$

providing 1×10×10×8×n×2×1×1=1600n compounds.

Both compound libraries, L1 and L2, of the above type are synthesized using solid phase techniques using the Multipin approach[24] such that each library contains 1600n compounds as 80n mixtures of 20 distinct, identifiable compounds. These 20 component mixtures are then placed separately into each of 80 wells of a 96 well plate (the other two lanes are used for control experiments) and then screened against a known quantity of the protease.

Thus it is an important part of the invention that regardless of the number of compounds contained in the two libraries L1 and L2 (e.g. in the preferred embodiment: 1600n, where n=any integer between 1 and 4) the libraries themselves are complementary and amenable to deconvolution without recourse to resynthesis. It is also an important part of the invention that the library matrix has been especially formatted so that the most important site pairings $P_2$ and $P_1$ for proteolytic enzymes can be identified immediately without recourse to resynthesis.

Those compounds of the type A-B-C-D-E-F-G that are the better substrates for the protease will be cleaved, and can be readily identified because the fluorescor, A, will be cleaved from its nearby quencher F, in a time dependent manner which can be easily quantified. The fluorescent quenching by F of A only occurs when the two are in nearby proximity, normally within 30 angstrom units.-Hence cleavage of a scissile bond (e.g. the scissile bond D-E) allows F to move further away from A and thus allow A to fluoresce when excited by light of the correct wavelength.

1. In this manner the most active compound can be rapidly identified without the need for further resynthesis and deconvolution. Moreover, the wells that show the most rapid development of fluorescence can also be analysed by mass spectrometry, since by comparison with the original mixture, the identity of the most efficient substrate can be found by its disappearance into its two component parts, e.g. A-B-C-D and E-F-G.

Hence the problem of library deconvolution can be overcome and the most active substrate for the enzyme can be rapidly identified.

In addition, after the initial treatment of the proteolytic enzyme with the library mixtures, L1 and L2, the residual enzymatic activity in each well can be quantified by the addition of the most potent fluorogenic substrate for the enzyme, S1, which is found in the 16xn compound library. Because of the nature of the library design this can be quickly prepared and purified. If there is no appearance of increased fluorescence with the known substrate, S1, then the presence of an enzyme inhibitor can be inferred, which again can be quickly identified without the need for resynthesis.

The general description of the library layout will now be described with reference to FIGS. 1 to 14.

For example, when n=1 and the library contains 1600 compounds, in the first column of the first row (A1) (FIG. 1) in the first plate (P1) of the library L1, (hereinafter designated as location A1,P1,L1) there will be one C component, $C_1$, one D component, $D_1$, the ten B components and the two E components ($E_1$ and $E_2$) (FIG. 2). In the tenth column of the first row (A10) in the first plate (P1) of the library L1, (hereinafter designated as location A10,P1, L1) there will be one C component, $C_{10}$, one D component, $D_1$, the ten B components and the two E components ($E_1$ and $E_2$). In the tenth column of the eighth row (H10) in the first plate (P1) of the library L1, (hereinafter designated as location H10, P1,L1) there will be one C component, $C_{10}$, one D component, $D_8$, the ten B components and the two E components ($E_1$ and $E_2$). Hence all 1600 components are present in the one plate, because the 80 wells each contain 20 components.

A second complementary library is synthesised as follows (FIG. 3). In the first column of the first row (A1) of the first plate (P1) of the library, L2, (hereinafter designated as location A1,P1,L2), there will be ten C components, two D components ($D_1$ and $D_2$), one B component, $B_1$, and one E component, $E_1$. In the tenth column of the first row (A10) of the first plate (P1) of the library, L2, (hereinafter designated as location A10,P1,L2), there will be ten C components, two D components ($D_1$ and $D_2$), one B component, $B_{10}$, and one E component, $E_1$. In the first column of the second row (B1) of the first plate (P1) of the library, L2, (hereinafter designated as location B1,P1,L2), there will be ten C components, two D components ($D_1$ and $D_2$), one B component, $B_1$, and one E component, $E_2$. In the tenth column of the second row (B10) of the first plate (P1) of the library, L2, (B10,P1,L2) there will be ten C components, two D components ($D_1$ and $D_2$), one B component, $B_{10}$, and one E component, $E_2$. Hence only the first two rows are used to accommodate 400 compounds in total.

In the first column of the first row (A1) of the second plate (P2) of the library, L2, (hereinafter designated as location A1,P2,L2), there will be ten C components, two D components ($D_3$ and $D_4$), one B component, $B_1$, and one E component, $E_1$ (FIG. 4). In the tenth column of the first row (A10) of the second plate (P2) of the library, L2, (hereinafter designated as location A10,P2,L2), there will be ten C components, two D components ($D_3$ and $D_4$), one B component, $B_{10}$, and one E component, $E_1$. In the first column of the second row ($B_1$) of the second plate (P2) of the library, L2, (hereinafter designated as location B1,P2, L2), there will be ten C components, two D components ($D_3$ and $D_4$), one B component, $B_1$, and one E component, $E_2$. In the tenth column of the second row (B10) of the second plate (P2) of the library, L2, (B10,P2,L2), there will be ten C components, two D components ($D_3$ and $D_4$), one B component, $B_{10}$, and one E component, $E_2$. Hence only the first two rows are used to accommodate 400 compounds in total.

In the first column of the first row (A1) of the third plate (P3) of the library, L2, (hereinafter designated as location A1,P3,L2), there will be ten C components, two D components ($D_5$ and $D_6$), one B component, $B_1$, and one E component, $E_1$ (FIG. 5). In the tenth column of the first row (A10) of the third plate (P3) of the library, L2, (hereinafter designated as location A10,P3,L2), there will be ten C components, two D components ($D_5$ and $D_6$), one B component, $B_{10}$, and one E component, $E_1$. In the first column of the second row ($B_1$) of the third plate (P3) of the library, L2, (hereinafter designated as location B1,P3,L2), there will be ten C components, two D components ($D_5$ and $D_6$), one B component, $B_1$, and one E component, $E_2$. In the tenth column of the second row (B10) of the third plate (P3) of the library, L2, (B10,P3,L2), there will be ten C components, two D components ($D_5$ and $D_6$), one B component, $B_{10}$, and one E component, $E_2$. Hence only the first two rows are used to accommodate 400 compounds in total.

In the first column of the first row (A1) of the fourth plate (P4) of the library, L2, (hereinafter designated as location A1,P4,L2), there will be ten C components, two D components ($D_7$ and $D_8$), one B component, $B_1$, and one E component, $E_1$ (FIG. 6). In the tenth column of the first row (A10) of the fourth plate (P4) of the library, L2, (hereinafter designated as location A10,P4,L2), there will be ten C components, two D components ($D_7$ and $D_8$), one B component, $B_{10}$, and one E component, $E_1$. In the first column of the second row (B1) of the fourth plate (P4) of the library, L2, (hereinafter designated as location B1,P4,L2), there will be ten C components, two D components ($D_7$ and $D_8$), one B component, $B_1$, and one E component, $E_2$. In the tenth column of the second row (B10) of the fourth plate (P4) of the library, L2, (B10,P4,L2), there will be ten C components, two D components ($D_7$ and $D_8$), one B component, $B_{10}$, and one E component, $E_2$. Hence only the first two rows are used to accommodate 400 compounds in total.

In this fashion two complementary libraries, L1 and L2 are prepared. In library, L1, each of the 80 of wells contains a mixture of 20 components providing 1600 compounds for screening. In library, L2, four plates are used in which only the first two rows are employed, providing 20 wells of 20 components per well per plate, and furnishing the same 1600 compounds as are present in library L1, but in a format in which no two compounds found together in library, L1, will be found together in library, L2.

Thus it is an important part of the invention that the compounds contained in the two libraries L1 and L2 are themselves complementary, in that any two compounds which are found together in a 20 component mixture in the same location (e.g. A1P1L1) in library L1, are not found together in any of the 20 component mixtures in any location of the library L2.

Thus, for example, with reference to the primary library P1 L1 of FIG. 2 and the secondary libraries P1 L2, P2 L2, P3 L2 and P4 L2 of FIGS. 3–6 it is possible to deconvolute an examplary sequence:

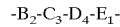

If this sequence is a substrate fluorescence will occur in P1 L1 at $C_3D_4$. This gives the information that the substrate is

If fluorescence occurs in P2 L2 at $B_2E_1$ it indicates a substrate

The confirmation of the substrate as

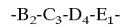

should be provided by non-fluorescence of P1 L2, P3 L2 and P4 L2 which all contain -$B_2$-$C_3$-X-$E_1$- where X is not $D_4$.

In practice it is likely that more than one sequence will result in a substrate. Information as to which positions B-C-D-E- are sensitive to change (i.e. require a specific group) and which are insensitive (i.e. can tolerate more than one choice of group) in the context of the whole sequence gives valuable SAR data which can be used to model and/or synthesise related compounds.

In analogous examples, where separately n=2, 3 or 4, extra plates are constructed in library L1 format to accommodate the component pairs $E_3$ and $E_4$ (n=2), $E_5$ and $E_6$ (n=3), and $E_7$ and $E_8$ (n=4), respectively. For the respective deconvolution libraries of the type, L2, the respective rows in the plates P1, P2, P3, and P4, are increasingly filled with the paired components $D_1$ and $D_2$, $D_3$ and $D_4$, and $D_5$ and $D_6$, and $D_7$ and $D_8$, respectively.

For example, when n=3, and the library contains 4800 compounds, in the first column of the first row (A1) in the first plate (P1) of the library L1, (hereinafter designated as location A1,P1,L1) there will be one C component, $C_1$, one D component, $D_1$, the ten B components and the two E components ($E_1$ and $E_2$). In the tenth column of the first row ($A_{10}$) in the first plate (P1) of the library L1, (hereinafter designated as location A10,P1,L1) there will be one C component, $C_{10}$, one D component, $D_1$, the ten B components and the two E components ($E_1$ and $E_2$). In the tenth column of the eighth row (H10) in the first plate (P1) of the library L1, (hereinafter designated as location H10,P1,L1) there will be one C component, $C_{10}$, one D component, $D_8$, the ten B components and the two E components ($E_1$ and $E_2$). Hence 1600 components are present in the one plate, because the 80 wells each contain 20 components.

In the first column of the first row (A1) in the second plate (P2) of the library L1, (hereinafter designated as location A1,P2,L1) there will be one C component, $C_1$, one D component, $D_1$, the ten B components and the two E components ($E_3$ and $E_4$) In the tenth column of the first row (A10) in the second plate (P2) of the library L1, (hereinafter designated as location A10,P2,L1) there will be one C component, $C_{10}$, one D component, $D_1$, the ten B components and the two E components ($E_3$ and $E_4$). In the tenth column of the eighth row (H10) in the second plate (P2) of the library L1, (hereinafter designated as location H10,P1,L1) there will be one C component, $C_{10}$, one D component, $D_8$, the ten B components and the two E components ($E_3$ and $E_4$). Hence 1600 components are present in the one plate, because the 80 wells each contain 20 components.

In the first column of the first row (A1) in the third plate (P3) of the library L1, (hereinafter designated as location A1,P3,L1) there will be one C component, $C_1$, one D component, $D_1$, the ten B components and the two E components ($E_5$ and $E_6$). In the tenth column of the first row (A10) in the third plate (P3) of the library L1, (hereinafter designated as location A10,P3,L1) there will be one C component, $C_{10}$, one D component, $D_1$, the ten B components and the two E components ($E_5$ and $E_6$). In the tenth column of the eighth row (H10) in the third plate (P3) of the library L1, (hereinafter designated as location H10,P3,L1) there will be one C component, $C_{10}$, one C component, $C_8$, the ten B components and the two E components ($E_5$ and $E_6$). Hence 1600 components are present in the one plate, because the 80 wells each contain 20 components. In total the three plate, P1, P2 and P3, contain 1600 compounds/plate 4800 compounds in total.

For example, when n=4, and the library contains 6400 compounds, in the first column of the first row (A1) in the first plate (P1) of the library L1, (hereinafter designated as location A1,P1,L1) there will be one C component, $C_1$, one D component, $D_1$, the ten B components and the two E components ($E_1$ and $E_2$) (FIG. 7). In the tenth column of the first row (A10) in the first plate ($P_1$) of the library L1, (hereinafter designated as location A10,P1,L1) there will be one C component, $C_{10}$, one D component, $D_1$, the ten B components and the two E components ($E_1$ and $E_2$). In the tenth column of the eighth row (H10) in the first plate (P1) of the library L1, (hereinafter designated as location H10,P1,L1) there will be one C component, $C_{10}$, one D component, $D_8$, the ten B components and the two E components ($E_1$ and $E_2$). Hence all 1600 components are present in the one plate, because the 80 wells each contain 20 components.

In the first column of the first row (A1) in the second plate (P2) of the library L1, (hereinafter designated as location A1,P2,L1) there will be one C component, $C_1$, one D component, $D_1$, the ten B components and the two E components ($E_3$ and $E_4$) (FIG. 8). In the tenth column of the first row (A10) in the second plate (P2) of the library L1, (hereinafter designated as location A10,P2,L1) there will be one C component, $C_{10}$, one D component, $D_1$, the ten B components and the two E components ($E_3$ and $E_4$). In the tenth column of the eighth row (H10) in the second plate (P2) of the library L1, (hereinafter designated as location H10,P2,L1) there will be-one C component, $C_{10}$, one D component, $D_8$, the ten B components and the two E components ($E_3$ and $E_4$).

In the first column of the first row (A1) in the third plate (P3) of the library L1, (hereinafter designated as location A1,P3,L1) there will be one C component, $C_1$, one D component, $D_1$, the ten B components and the two E components ($E_5$ and $E_6$) (FIG. 9). In the tenth column of the first row (A10) in the third plate (P3) of the library L1, (hereinafter designated as location A10,P3,L1) there will be one C component, $C_{10}$, one D component, $D_1$, the ten B components and the two E components ($E_5$ and $E_6$). In the tenth column of the eighth row (H10) in the third plate (P3) of the library L1, (hereinafter designated as location H10, P3,L1) there will be one C component, $C_{10}$, one D component, $D_8$, the ten B components and the two E components ($E_5$ and $E_6$).

In the first column of the first row (A1) in the fourth plate (P4) of the library L1, (hereinafter designated as location A1,P4,L1) there will be one C component, $C_1$, one D component, $D_1$, the ten B components and the two E components ($E_7$ and $E_8$) (FIG. 10). Likewise, in the tenth column of the first row (A10) in the fourth plate (P4) of the library L1, (hereinafter designated as location A10,P4,L1) there will be one C component, $C_{10}$, one D component, $D_1$, the ten B components and the two E components ($E_7$ and $E_8$). In the tenth column of the eighth row (H10) in the fourth plate (P4) of the library L1, (hereinafter designated as location H10,P4,L1) there will be one C component, $C_{10}$, one D component, $D_8$, the ten B components and the two E components ($E_7$ and $E_8$).

A second complementary library is synthesised as follows. In the first column of the first row (A1) of the first plate (P1) of the library, L2, (hereinafter designated as location A1,P1,L2), there will be ten C components, two D components ($D_1$ and $D_2$), one B component, $B_1$, and one E component, E1 (FIG. 11). In the tenth column of the first row (A10) of the first plate (P1) of the library, L2, (hereinafter designated as location A10,P1,L2), there will be the ten C components, two D components ($D_1$ and $D_2$), one B component, $B_{10}$, and one E component, $E_1$. In the first column of the eighth row (H1) of the first plate (P1) of the library, L2, (hereinafter designated as location H1,P1,L2), there will be the ten C components, two D components ($D_1$ and $D_2$), one B component, $B_1$, and one E component, $E_8$. In the tenth column of the eighth row (H10) of the first plate (P1) of the library, L2, (H10,P1,L2) there will be the ten C components, two D components ($D_1$ and $D_2$), one B component, $B_{10}$, and one E component, $E_8$. Hence the matrix containing all ten columns and all eight rows are used to accommodate 1600 compounds in total.

In the first column of the first row (A1) of the second plate (P2) of the library, L2, (hereinafter designated as location A1,P2,L2), there will be ten C components, two D components ($D_3$ and $D_4$), one B component, $B_1$, and one E component, $E_1$ (FIG. 12). In the tenth column of the first row (A10) of the second plate (P2) of the library, L2, (hereinafter designated as location A10,P2,L2), there will be ten C components, two D components ($D_3$ and $D_4$), one B component, $B_{10}$, and one E component, $E_1$. In the first column of the second row (B1) of the second plate (P2) of the library, L2, (hereinafter designated as location B1,P2, L2), there will be ten C components, two D components ($D_3$ and $D_4$), one B component, $B_1$, and one E component, $E_2$. In the tenth column of the eighth row (H10) of the second plate (P2) of the library, L2, (H10,P2,L2), there will be ten C components, two D components ($D_3$ and $D_4$), one B component, $B_{10}$, and one E component, $E_8$.

In the first column of the first row (A1) of the third plate (P3) of the library, L2, (hereinafter designated as location A1,P3,L2), there will be ten C components, two D components ($D_5$ and $D_6$), one B component, $B_1$, and one E component, $E_1$ (FIG. 13). In the tenth column of the first row (A10) of the third plate (P3) of the library, L2, (hereinafter designated as location A10,P3,L2), there will be ten C components, two D components ($D_5$ and $D_6$), one B component, $B_{10}$, and one E component, $E_1$. In the first column of the second row (B1) of the third plate (P3) of is the library, L2, (hereinafter designated as location B1,P3, L2), there will be ten C components, two D components ($D_5$ and $D_6$), one B component, $B_1$, and one E component, $E_2$. In the tenth column of the eighth row ($H_{10}$) of the third plate (P3) of the library, L2, (H10,P3,L2), there will be ten C components, two D components ($D_5$ and $D_6$), one B component, $B_{10}$, and one E component, $E_8$.

In the first column of the first row (A1) of the fourth plate (P4) of the library, L2, (hereinafter designated as location A1,P4,L2), there will be ten C components, two D components ($D_7$ and $D_8$), one B component, $B_1$, and one E component, $E_1$ (FIG. 14). In the tenth column of the first row ($A_{10}$) of the fourth plate (P4) of the library, L2, (hereinafter designated as location A10,P4,L2), there will be ten C components, two D components ($D_7$ and $D_8$), one B component, $B_{10}$, and one E component, $E_1$. In the first column of the second row (B1) of the fourth plate (P4) of the library, L2, (hereinafter designated as location B1,P4,L2), there will be ten C components, two D components ($D_7$ and $D_8$), one B component, $B_1$, and one E component, $E_2$. In the tenth column of the eighth row (H10) of the fourth plate (P4) of the library, L2, (H10,P4,L2), there will be ten C components, two D components ($D_7$ and $D_8$), one B component, $B_{10}$, and one E component, $E_8$.

It will be apparent to those skilled in the art that the synthesis of two orthogonal sets of mixtures in solution providing two complementary FRET libraries indexed in two dimensions for autodeconvolution does not require the currently preferred arrangement -$B_{1-10}$-$C_{1-10}$-$D_{1-8}$-$E_{1-8}$-.

The general concept of two orthogonal sets of mixtures indexed in two dimensions can be applied to various permutations of numbers of wells, plate layout, number of permutations per mixture etc.

A numerical interrelationship can be defined as follows:
General Deconvolution Formulae $$\text{-Bb-Cc-Dd-}n(\text{Ee})\text{-} \tag{I}$$

1) Primary and Secondary plates preferably have the same number of compounds per well [X]: otherwise there are two values, having $X_p$ and $X_s$ respectively.

2) The primary library comprises [np] plates.

If Rp.Cp=Rs.Cs, then the number of plates in the secondary library is also [np]. If not, the number of plates in the secondary library [ns] is:

$$ns=Rp.Cp/Rs.Cs.np$$

e.g. A primary library of np=4, Rp=8, Cp=10 can be set out in an Rs=4, Cs=5 secondary library with the number of plates equal to:

$$: ns=8\times10/4\times5.np=16 \text{ plates.}$$

Number of compounds per well $$\text{-Bb-Cc-Dd-np(Ee)-} \tag{1}$$

Number of possible combinations [k] is given by:

$$k=b.c.d.np.e \tag{2}$$

When number of wells on a plate=[N], number of compounds per well=[X] and number of plates=[np]:

$$k=X.N.np \tag{3}$$

However, number of wells [N] is also defined by the number of rows [Rp] and number of columns [Cp]:

$$N=Rp.Cp \tag{4}$$

Combining (3) and (4):

$$k=X.Rp.Cp.np \tag{5}$$

Combining (2) and (5):

$$b.c.d.np.e=X.Rp.Cp.np \tag{6}$$

Cancelling [np] from both sides of the equation:

$$b.c.d.e=X.Rp.Cp \tag{7}$$

Two of the variables (e.g. b.c) on the left side of the equation must each be equal in number to the number of columns [Cp], whilst a remaining variable (e.g. d) on the left side must be equal in number to the number of rows [Rp]. So:

$$[cp]^2.Rp.e=X.Rp.Cp \tag{8}$$

Cancelling [Cp] and [Rp] from both sides of the equation:

$$Cp.e=X \tag{9}$$

where [e] is the number of variants along a fixed row; and if Rp=Cp, then Rp.e=X.

EXAMPLE for a 10×10×8×8 format over 4 plates:

$$np.e=8=>e=2$$

$$10\times2=X$$

$$X=20.$$

From an understanding of the general deconvolution formulae shown above, those skilled in the art will readily appreciate that the advantageous results of self-deconvolution according to the invention are obtainable utilising a number of different arrangements of wells, plate layouts, mixtures etc and that such variants on the preferred embodiment illustrated herein are intended to be within the scope of the present invention.

The FRET strategy is based on the synthesis of two orthogonal sets of mixtures in solution. These solutions are each indexed in two dimensions. Thus the data from, for example, a protease scan identifies the most active compounds without the need for decoding or resynthesis. The positional preferences of sub-units (in this case amino acids) are optimised with respect to all other variant positions simultaneously. The synergistic relationship between all four positions is realised and both positive, beneficial and negative, deactivating data are generated. This leads to families (sub-populations) of substrates and their sub-unit preferences. The data can be fed into molecular modelling programs to generate pharmacophoric descriptors that encompass both the desirable features (from the positive data) and indicate undesirable interactions (from the negative data sets). Note that a one dimensional scan only indicates one position at a time as 'most active' and does not explore the synergistic relationship between positions.

The invention will now be described by reference to the following examples.

Example 1

In this Example the proteolytic enzyme of interest is Der P1, which is found in house dust mite faeces. The example illustrates the synthesis of a number of FRET compounds in which the suitable bond is an unsubstituted amide bond, their use as a library for screening for potential substrates of Der P1, and subsequent identification and synthesis of active inhibitors of the enzyme.

Purification of Der pI.

Crude mite extract (~100 mg, SmithKline-Beecham, U.K) was dissolved in 5 mL Phosphate Buffered Saline (PBS; 50 mM potassium phosphate; pH 7.4 containing 150 mM NaCl Der pI was purified by affinity column chromatography using 4Cl antibody (indoor Biotechnology, Deeside, U.K.) The crude preparation was mixed with ~2 mL of affinity resin for 2 h at 4° C. and then washed with 2–3 volumes of PBS. Elution of bound protein was carried out using 5 mM glycine containing 50% (v/v) ethylene glycol. Fractions(2.2 mL) were collected and neutralised with 0.8 mL of 0.2 M sodium phosphate buffer, pH 7.0. The fractions were pooled and dialysed overnight against 4 L PBS followed by a second dialysis against 2 L PBS for 2–3 h. The total protein was concentrated as required by ultrafiltration (MacroSep; Flowgen, U.K.)

Synthesis of compounds

The compounds were synthesised using the Multipin approach[25,26] using Fmoc-Rink amide Macro crowns (Chiron Mimotypes Pty., Ltd., 11 Duerdin Street, Clayton Victoria 3168, Australia) with a loading of 7 $\mu$Moles.

The amino acid residues of each of the compounds were linked using amide bonds in a suitable form. The coupling chemistry employed is similar to that reported in the literature[27] for fluorenylmethoxycarbonyl protected amino acids and activated pentafluorophenyl esters, in which the side-chains are protected using acid labile protecting groups known to those skilled in the art, such as Boc- (for the —$NH_2$ of Lysine, —$NH_2$ of anthranilic acid and guanidino of arginine), tBu- (for the —OH groups of serine, threonine and tyrosine), t-Bu for the —COOH group of Aspartic acid and Glutamic acid, Trityl- (for the Amide of Asparagine and Glutamine, and the amine functionality of the Histidine ring.

The N-α-fluorenylmethoxycarbonyl protecting group of the coupled residues were cleaved using 20% piperidine in dimethylformamide (DMF) for 30 minutes at 20° C. The coupling reactions for the free acids such as Boc-ABz-OH (Boc-2-aminobenzoic acid), and Fmoc-(3-nitro)tyrosine-OH were accomplished using 10 equivalents of a mixture of the free acid (1 eq.):TBTU (0.98 eq.):HOBt (0.98 eq.):N-methylmorpholine (1.96 eq.) in dimethylformamide (500 $\mu$L) as solvent for 5 hours at 20° C. The other amino acids were coupled as their pentafluorophenyl esters[26] for 2–6 hours.

Hence, in order to couple approximately equal ratios of each component in the mixture of the derivatised amino acids as their pentafluorophenyl esters, a solution of a total of 0.98 equivalents (relative to the amino group loading on the crown) of the mixture of amino acid pentafluorophenyl esters:HOBT (1 eq.) in DMF (500 $\mu$L) were coupled for 16 hours at 20° C. The pins were then washed well with DMF and then recoupled using the same mixture under the same conditions. A third coupling of 10 equivalents (relative to the amino group loading of the crown) for 2 hours in DMF was performed using this coupling protocol with equimolar mixtures of the derivatised pentafluorophenyl esters of the amino acids in slightly less than 1 equivalent, it is possible to obtain approximately equal amounts of the coupled products to the crown. In this fashion the libraries are constructed with 20 compounds present on each crown. The compounds were cleaved from the crowns directly into the 80 designated wells of the desired 96 well plate. In the cleavage protocol each crown was treated with a mixture (600 $\mu$L) containing trifluoroacetic acid (95%), triethylsilane (5%) for 2 hours at 20° C. The crowns were then washed with trifluoroacetic acid (500 $\mu$L) and this was then combined with the cleavage solution.

The Fmoc-Rink amide Macro crowns (Chiron Mimotypes Pty., Ltd., 11 Duerdin Street, Clayton Victoria 3168, Australia) at 7 $\mu$Mol loading per crown, were coupled with a 10 fold excess of a mixture containing L-Fmoc-Asp(O-t-Bu)-OH (1 eq) using TBTU (0.98 eq) and N-methylmorpholine (1.96 eq.) in the presence of HOBt (0.98 eq.) in DMF at 0.14M concentration. After deblocking of the Fmoc group with 20% piperidine in DMF for 30 minutes and subsequent washing with DMF and then methanol, coupling of the Fmoc-(3-nitro)tyrosine-OH was accomplished using 10 equivalents of a mixture of the Fmoc-(3-nitro)tyrosine-OH (1 eq.):TBTU (0.98 eq.):HOBt (0.98 eq.): N-methylmorpholine (1.96 eq.) in dimethylformamide as solvent at 0.14 M concentration for 5 hours at 20° C. Removal of the Fmoc is group (vide infra) was followed by coupling of the mixtures of amino acids in the ratios outlined and under the conditions described (vide infra).

In a particular example the amino acids comprising group B include Ala, Val, Leu, Ser, Asn, Gln, Glu, Lys, Phe, Pro. The amino acids comprising group C include Ala, Val, Leu, Ser, Asn, Gln, Glu, Lys, Phe, Pro. The amino acids comprising group D include Ala, Val, Ile, Leu, Nle, Ser, Glu, Phe. For n=4, the amino acids comprising group E include Ala, Val, Ile, Leu, Nle, Ser, Glu, Phe. Otherwise any selection from the amino acids can be made for n=1, 2, or 3.

The plates containing the combined cleavage solutions and were then evaporated to dryness to yield the component mixtures using a rotary centrifuge ("SPEEDVAC", Savant Instruments Inc., Farmingdale, N.Y.) at 800 rpm for 1 hour at 20° C. under a reduced pressure of $10^{-2}$ mmHg. Each component was then transferred to the final mother plate using a (50%:45%:5%) mixture of acetonitrile:water:acetic acid. The plates were then lyophilised to dryness using at 20° C. under a reduced pressure of $10^{-2}$ mmHg, and then stored at −20° C. In this fashion libraries of the type shown in FIGS. 2–14 were prepared.

In further detail, the Multipin approach which was employed is described below:

Multipin Synthesis Of Potential Substrates of Der pI

The 'Chiron' multipin kit consists of a standard 8×12 pin holder containing 96 'pin stems' to which are reversibly attached 'crowns'. The 'crowns' provide a reactive polymer surface upon which a growing peptide is is anchored during solid phase peptide synthesis. Each crown (the equivalent of the peptide-resin in standard solid phase synthesis) can be considered to be an independent reactor by performing simultaneous synthesis in individual 1 mL wells of industry standard 96 well plates. Each well, and thus each crown, can be charged with a unique set of reagents providing unique sequences to each crown. Common steps such as washing or removal of Nα protection can be performed concomitantly.

Synthesis is based upon the use of Nα-fluorenylmethyloxycarbonyl (Fmoc) protected amino acids. Side-chains of tri-functional amino acids are protected with acid labile groups such as trityl or tert-butyl. The addition of amino-acid residues to the growing peptide chain, a process termed 'coupling' proceeds through the utilisation of pre-formed pentafluorophenyl (pfp) esters or activation of the free acid, using the reagents HBTU or BOP in the presence of tertiary base (NMM) and HOBt as catalyst.

The experimental techniques used are fully documented (Maeji, N. J. Bray, A. M. Valerio, R. M. and Wang, W., *Peptide Research*, 8(1), 33–38, 1995 and Valerio, R. M. Bray, A. M. and Maeji, N. J. *Int. J. Pept. Prot. Res*, 44, 158–165, 1994) and the main steps are briefly as follows.

General Methods

Preparation of Multipin Assembly

Whilst wearing standard plastic gloves, Fmoc-Rink Amide derivitized macrocrowns are assembled (simply clipped) onto stems and slotted into the 8×12 stem holder in the desired pattern for synthesis.

Removal of Nα-Fmoc Protection

A 250 mL solvent resistant bath is charged with 200 ml of a 20% piperidine/DMF solution. The multipin assembly is added and deprotection allowed to proceed for 30 minutes. The assembly is then removed and excess solvent removed by brief shaking. The assembly is then washed consecutively with (200 mL each), DMF (5 mins) and MeOH (5 mins, 2 mins, 2 mins) and left to air dry for 15 mins.

Quantitative UV Measurement of Fmoc Chromophore Release

A 1 cm path length UV cell is charged with 1.2 mL of a 20% piperidine/DMF solution and used to zero the absorbance of the UV spectrometer at a wavelength of 290 nm. A UV standard is then prepared consisting of 5.0 mg Fmoc-Asp(OBut)-Pepsyn KA (0.08 mmol/g) in 3.2 mL of a 20% piperidine/DMF solution. This standard gives $Abs_{290}$=0.55–0.65 (at RT). An aliquot of the multipin deprotection solution is then diluted as appropriate to give a theoretical $Abs_{290}$=0.6, and this value compared with the actual experimentally measured absorbance showing the efficiency of previous coupling reaction.

Coupling of Amino-acid Residues

Whilst the multipin assembly is drying, the appropriate Nα-Fmoc amino acid pfp esters (10 equivalents calculated from the loading of each crown) and HOBt (10 equivalents) required for the particular round of coupling are accurately weighed into suitable containers. Alternatively, the appropriate Nα-Fmoc amino acids (10 equivalents calculated from the loading of each crown), desired coupling agent e.g. HBTU (9.9 equivalents calculated from the loading of each crown) and activation e.g. HOBt (9.9 equivalents calculated from the loading of each crown), NMM (19.9 equivalents calculated from the loading of each crown) are accurately weighed into suitable containers.

The protected and activated Fmoc amino acid derivatives are then dissolved in DMF (500 μl for each macrocrown, e.g. for 20 macrocrowns, 20×10 eq×7 mmoles of derivative would be dissolved in 10 000 μL DMF). The appropriate derivatives are then dispensed to the appropriate wells ready for commencement of the 'coupling cycle'. As a standard, coupling reactions are allowed to proceed for 2–6 hours (depending upon nature of coupling e.g. Ala to Ala 2 hours Val to Leu 6 hours.

When coupling Fmoc amino-acid pentafluorophenyl esters, 10 eq of derivative in DMF (400 μl) with bromophenol blue stock solution (100 μl) is used for each macrocrown. This allows monitoring of the progress of the acylation reaction through the disappearance of the deep blue coloration of bromophenol blue in the presence of unreacted amine to a pale yellow upon completion of acylation.

Preparation of Bromophenol Blue Stock Solution

Bromophenol blue (20 mg) is dissolved in DMF (50 mL) and HOBt (10 mg) added.

Washing Following Coupling

If a 20% piperidine/DMF deprotection is to immediately follow the coupling cycle, then the multipin assembly is briefly shaken to remove excess solvent washed consecutively with (200 mL each), MeOH (5 mins) and DMF (5 mins) and deprotected (see above). If the multipin assembly is to be stored, then a full washing cycle consisting brief shaking then consecutive washes with (200 mL each), DMF (5 mins) and MeOH (5 mins, 2 mins, 2 mins) is performed.

Acidolytic Mediated Cleavage of Peptide-Pin Assembly

Acid mediated cleavage protocols are strictly performed in a fume hood. A polystyrene 96 well plate (1 mL/well) is labelled, then the tare weight measured to the nearest mg. Appropriate wells are then charged with a trifluoroacetic acid/triethylsilane (95:5, v/v, 600 μl) cleavage solution, in a pattern corresponding to that of the multipin assembly to be cleaved.

The multipin assembly is added, the entire construct covered in tin foil and left for 2 hrs. The multipin assembly in then added to another polystyrene 96 well plate (1 mL/well) containing trifluoroacetic acid/triethylsilane (95:5, v/v, 600 μl) (as above) for 5 mins.

The cleaved assembly is washed with DMF (200 μL, 5 mins), MeOH (200 μL, 5 mins), the spent crowns removed and discarded, the stems removed and washed by sonication in methanol (1 hr, RT).

Work up of Cleaved Peptides

The primary polystyrene cleavage plate (2 hr cleavage) and the secondary polystyrene plate (5 min wash) (see above) are then placed in the SpeedVac and the solvents removed (minimum drying rate) for 90 mins.

The contents of the secondary polystyrene plate (see above) are transferred to their corresponding wells on the primary plate using an acetonitrile/water/acetic acid (50:45:5, v/v/v) solution (3×150 μl) and the spent secondary plate discarded.

Analysis of Products 1.0 μl of each well (see above) is diluted to 400 μl with 0.1%aq TFA and analysed by HPLC-MS. Column Vydac C4 (214TP52, narrowbore, 21×250 mm). Eluents:–Solvent A=0.1%aq trifluoroacetic acid, Solvent B=acetonitrile/10%A. Gradient:–10–90% B in A over 27 mins, 250 ml/min, 215 nm UV detection. The individual substrates described below were prepared by the above methods and shown by HPLC-MS to be >95% with the correct mass.

19

Final Lyophilisation of Peptides

The primary polystyrene plate (plus the washings from the secondary plate) is covered with tin foil, held to the plate with an elastic band. A pin prick is placed in the foil directly above each well and the plate placed at −80° C. for 30 mins. The plate is then lyophilised on the 'Heto freeze drier' overnight. Where appropriate individual peptides were then weighed and dissolved to 10 mM stock solutions in DMSO prior to biological screening. Alternatively the 20 component mixture is weighed and the peptide/20 component ratio is calculated.

Further coupling of amino acid residues was carried out according to the multipin approach described above. Whilst the multipin assembly was drying, the appropriate Nα-Fmoc amino acids (10 equivalents calculated from the loading of each crown), HATU coupling agent (9.9 equivalents calculated from the loading of each crown), HOAt catalyst (9.9 equivalents calculated from the loading of each crown) and DIPEA (19.9 equivalents calculated from the loading of each crown)were accurately weighed into suitable containers.

The protected Nα-Fmoc amino acids and coupling agents were then dissolved in DMF (500 μl for each macrocrown) and activated by the addition of DIPEA. The appropriate derivatives were then dipensed to their appropriate wells and as standard coupling to each macro crown was allowed to proceed for 2 hours.

When coupling particularly hindered amino acid residues such as N-Methyl, Cα-Methyl or unusual amino acids (whose coupling efficiency is unknown) the coupling reaction was repeated, as standard, for a further 2 hours.

Substrates for Der pI

Using the general techniques described above, the following compounds were prepared and assayed as potential substrates against Der pI purified as described above.

| Peptide [SEQ ID Nos. 1–76] | Measured $K_m$ (μM) |
|---|---|
| Abz-Val-Ala-Nle-Ser-Tyr(NO$_2$)-Asp-NH$_2$ | 12 |
| H-Val-Ala-Nle-Ser-TyrNO$_2$-Asp-NH$_2$ | NS |
| H-Ala-Nle-Ser-Tyr(NO$_2$)-Asp-NH$_2$ | NS |
| Ac-Val-Ala-Nle-Ser-Tyr(NO$_2$)-Asp-NH$_2$ | NS |
| H-Val-Ala-Nle-Ser-Tyr(NO$_2$)-NH$_2$ | NS |
| H-Ala-Nle-Ser-Tyr(NO$_2$)-Asp-NH$_2$ | NS |
| Ac-Val-Ala-Nle-Ser-Tyr(NO$_2$)-NH$_2$ | NS |
| Abz-Val-Ala-Nle-Ser-Tyr(NO$_2$)-NH$_2$ | NM |
| Abz-Val-Ala-Nle-Ser-NH$_2$ | NM |
| Abz-Val-Ala-Nle-Ser-Phe-Asp-NH$_2$ | NM |
| Abz-Val-Ala-Nle-Ser-Tyr-Asp-NH$_2$ | NM |
| Abz-Val-Ala-Nle-Ser-Ala-Asp-NH$_2$ | NM |
| Abz-Val-Ala-Nle-Ser-Lys-Asp-NH$_2$ | NM |
| Abz-Val-Ala-Nle-Ser-eAHA-Asp-NH$_2$ | NM |
| Abz-Ala-Nle-Ser-Tyr(NO$_2$)-Asp-NH$_2$ | NM |
| Abz-Nle-Ser-Tyr(NO$_2$)-Asp-NH$_2$ | NS |
| Bz-Val-Ala-Nle-ser-Tyr(NO$_2$)-NH$_2$ | NM[a] |
| Bz(2-carboxy)-Val-Ala-Nle-Ser-Tyr(NO$_2$)-NH$_2$ | NM[a] |
| Chex-Val-Ala-Nle-Ser-Tyr(NO$_2$)-NH$_2$ | NM[a] |
| n-Bu-Val-Ala-Nle-Ser-Tyr(NO$_2$)-NH$_2$ | NM[a] |
| Piv-Val-Ala-Nle-Ser-Tyr(NO$_2$)-NH$_2$ | NM[a] |
| Bz-Val-Ala-Nle-Ser-Tyr(NO$_2$)-NH$_2$ | NM[a] |
| Abz-Val-Ala-Lys-Ser-Tyr(NO$_2$)-Asp-NH$_2$ | 14 |
| Abz-Val-Ala-Gln-Ser-Tyr(NO$_2$)-Asp-NH$_2$ | 6 |
| Abz-Val-Ala-Thr-Ser-Tyr(NO$_2$)-Asp-NH$_2$ | 6 |
| Abz-Val-Ala-hLeu-Ser-Tyr(NO$_2$)-Asp-NH$_2$ | 4 |
| Abz-Val-Ala-Cha-Ser-Tyr(NO$_2$)-Asp-NH$_2$ | 5 |
| Abz-Val-Ala-His-Ser-Tyr(NO$_2$)-Asp-NH$_2$ | >20 |
| Abz-Val-Ala-ACH-Ser-Tyr(NO$_2$)-Asp-NH$_2$ | NS |
| Abz-Val-Ala-DNle-Ser-Tyr(NO$_2$)-Asp-NH$_2$ | NS |
| Abz-Val-Ala-3pyr-Ser-Tyr(NO$_2$)-Asp-NH$_2$ | 10 |
| Abz-Val-Ala-Hyp-Ser-Tyr(NO$_2$)-Asp-NH$_2$ | NS |

20

-continued

| Peptide [SEQ ID Nos. 1–76] | Measured $K_m$ (μM) |
|---|---|
| Abz-Val-Ala-ACP-Ser-Tyr(NO$_2$)-Asp-NH$_2$ | NS |
| Abz-Val-Lys-hLeu-Ser-Tyr(NO$_2$)-Asp-NH$_2$ | 35 |
| Abz-Val-DAla-hLeu-Ser-Tyr(NO$_2$)-Asp-NH$_2$ | NS |
| Abz-Val-Tic-hLeu-Ser-Tyr(NO$_2$)-Asp-NH$_2$ | NS |
| Abz-Val-ACH-hLeu-Ser-Tyr(NO$_2$)-Asp-NH$_2$ | NS |
| Abz-Val-Met(O)-hLeu-Ser-Tyr(NO$_2$)-Asp-NH$_2$ | 35 |
| Abz-Val-2Nal-hLeu-Ser-Tyr(NO$_2$)-Asp-NH$_2$ | NS |
| Abz-Val-ACP-hLeu-Ser-Tyr(NO$_2$)-Asp-NH$_2$ | NS |
| Abz-Val-DLys-hLeu-Ser-Tyr(NO$_2$)-Asp-NH$_2$ | NS |
| Abz-Val-DGln-hLeu-Ser-Tyr(NO$_2$)-Asp-NH$_2$ | NS |
| Abz-Val-3pyr-hLeu-Ser-Tyr(NO$_2$)-Asp-NH$_2$ | NS |
| Abz-Val-Cha-hLeu-Ser-Tyr(NO$_2$)-Asp-NH$_2$ | NS |
| Abz-DVal-Ala-hLeu-Ser-Tyr(NO$_2$)-Asp-NH$_2$ | NS |
| Abz-Gln-Ala-hLeu-Ser-Tyr(NO$_2$)-Asp-NH$_2$ | 12 |
| Abz-Lys-Ala-hLeu-Ser-Tyr(NO$_2$)-Asp-NH$_2$ | >15 |
| Abz-Tic-Ala-hLeu-Ser-Tyr(NO$_2$)-Asp-NH$_2$ | NS |
| Abz-ACH-Ala-hLeu-Ser-Tyr(NO$_2$)-Asp-NH$_2$ | NS |
| Abz-Met(O)-Ala-hLeu-Ser-Tyr(NO$_2$)-Asp-NH$_2$ | 20 |
| Abz-3pyr-Ala-hLeu-Ser-Tyr(NO$_2$)-Asp-NH$_2$ | >10 |
| Abz-2Nal-Ala-hLeu-Ser-Tyr(NO$_2$)-Asp-NH$_2$ | 15 |
| Abz-Leu-Ala-hLeu-Ser-Tyr(NO$_2$)-Asp-NH$_2$ | 18 |
| Abz-Cha-Ala-hLeu-Ser-Tyr(NO$_2$)-Asp-NH$_2$ | 9 |
| Abz-Bip-Ala-hLeu-Ser-Tyr(NO$_2$)-Asp-NH$_2$ | 2.5 |
| Abz-Bip-Ala-hLeu-Tyr-Tyr(NO$_2$)-Asp-NH$_2$ | 3 |
| Abz-Bip-Ala-hLeu-Leu-Tyr(NO$_2$)-Asp-NH$_2$ | 3.7 |
| Abz-Bip-Ala-hLeu-Lys-Tyr(NO$_2$)-Asp-NH$_2$ | 2 |
| Abz-Bip-Ala-hLeu-Asp-Tyr(NO$_2$)-Asp-NH$_2$ | 5.0 |
| Abz-Bip-Ala-hLeu-Abu-Tyr(NO$_2$)-Asp-NH$_2$ | 1.7 |
| Abz-Bip-Ala-hLeu-Cha-Tyr(NO$_2$)-Asp-NH$_2$ | 2.5 |
| Abz-Bip-Ala-hLeu-Met(O)-Tyr(NO$_2$)-Asp-NH$_2$ | 5 |
| Abz-Bip-Ala-hLeu-Thr-Tyr(NO$_2$)-Asp-NH$_2$ | 2.5 |
| Abz-Bip-Ala-hLeu-3pyr-Tyr(NO$_2$)-Asp-NH$_2$ | 4 |
| Abz-Bip-Ala-hLeu-Bu$^t$Gly-Tyr(NO$_2$)-Asp-NH$_2$ | 4 |
| Abz-Bip-Ala-hLeu-Hyp-Tyr(NO$_2$)-Asp-NH$_2$ | 4 |
| Abz-Phe-Val-Ala-Nle-Ser-Tyr(NO$_2$)-Asp-NH$_2$ | NM |
| Abz-3.Pyr-Val-Ala-Nle-Ser-Tyr(NO$_2$)-Asp-NH$_2$ | NM |
| Abz-1.Naph-Val-Ala-Nle-Ser-Tyr(NO$_2$)-Asp-NH$_2$ | 17 |
| Abz-2.Naph-Val-Ala-Nle-Ser-Tyr(NO$_2$)-Asp-NH$_2$ | NM |
| Abz-Tyr-Val-Ala-Nle-Ser-Tyr(NO$_2$)-Asp-NH$_2$ | NM |
| Abz-Bip-Val-Ala-Nle-Ser-Tyr(NO$_2$)-Asp-NH$_2$ | 10 |
| Abz-Lys-Val-Ala-Nle-Ser-Tyr(NO$_2$)-Asp-NH$_2$ | 15 |
| Abz-Glu-Val-Ala-Nle-Ser-Tyr(NO$_2$)-Asp-NH$_2$ | 20 |
| Abz-Leu-Val-Ala-Nle-Ser-Tyr(NO$_2$)-Asp-NH$_2$ | NM |
| Abz-Hyp-Val-Ala-Nle-Ser-Tyr(NO$_2$)-Asp-NH$_2$ | NS |

NS indicates that the peptide was not hydrolysed by Der pI.
NM indicated that the peptide was a substrate for Der pI, but the $K_m$ was not measured.
NM[a] indicates that the peptide was a substrate for Der pI, and its cleavage was followed by HPLC-MS showing hydrolysis to occur between-Nle-Ser-.
Ranked in order of cleavage rate: -Bz > n-But > Piv > Bz(2-carboxy) > Abz.

Coupling of amino acid residues was carried out according to the multipin approach described above. Whilst the multipin assembly was drying, the appropriate Nα-Fmoc amino acids (10 equivalents calculated from the loading of each crown), HATU coupling agent (9.9 equivalents calculated from the loading of each crown), HOAt catalyst (9.9 equivalents calculated from the loading of each crown) and DIPEA (19.9 equivalents calculated from the loading of each crown) were accurately weighed into suitable containers.

The protected Nα-Fmoc amino acids and coupling agents were then dissolved in DMF (500 μl for each macrocrown) and activated by the addition of DIPEA. The appropriate derivatives were then dispensed to their appropriate wells and standard coupling to each macrocrown was allowed to proceed for 2 hours.

When coupling particularly hindered amino acid residues such as N-Methyl, Cα-Methyl or unusual amino acids (whose coupling efficiency is unknown) the coupling reaction was repeated, as standard, for a further 2 hours.

The following sequences were synthesised in this way:
Peptide Sequence [SEQ ID Nos. 77–85] Measured Km(μM)

| Peptide Sequence [SEQ ID Nos. 77–85] | Measured Km (μM) |
|---|---|
| Abz-Val-Ala-(NMe)Nle-Ser-Tyr(NO$_2$)-Asp-NH$_2$ | NS |
| Abz-Val-(NMe)Ala-Nle-Ser-Tyr(NO$_2$)-Asp-NH$_2$ | NS |
| Abz-Val-Ala-Aib-Ser-Tyr(NO$_2$)-Asp-NH$_2$ | NS |
| Abz-Val-Aib-Nle-Ser-Tyr(NO$_2$)-Asp-NH$_2$ | NS |
| Abz-Deg-Ala-Nle-Ser-Tyr(NO$_2$)-Asp-NH$_2$ | NS |
| nBu-D.Ser-D.Nle-D.Ala-D.Val-p.Aba-NH$_2$ | NS |
| Bz-Val-Ala-Statine-Ser-eAha-NH$_2$ | NS |
| Abz-p.Aba-Nle-Ser-Tyr(NO$_2$)-Asp-NH$_2$ | NS |
| Abz-Cmpi-Nle-Ser-Tyr(NO$_2$)-Asp-NH$_2$ | NS |

NS—Not Substrate: Not hydrolysed by Der pI
NM—Substrate but not measured: Substrate for Der pI but not measured.

Assay Procedure

Each mixture of 20 compounds in the libraries of the apparatus described herein was screened at a concentration of 1.0 μM per compound in an assay against the cysteinyl protease Der pI. The most active wells were identified by the rate of emission of fluorescence at 420 nm when the samples were irradiated at 320 nm. An analysis of the two complementary libraries showed that the best substrates for the enzyme were:

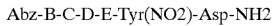

Abz-B-C-D-E-Tyr(NO2)-Asp-NH2

Where
B=Valine>Alanine, Glutamine, Leucine, Phenylalanine
C=Alanine>>Glutamine, or Lysine.
D=Leucine, Norleucine or Alanine>Serine
E=Serine
The best substrate was:
SEQ ID no:1 Abz-Val-Ala-Nle-Ser-Tyr(NO$_2$)-Asp-NH$_2$ This compound was then resynthesised as a single component using the peptide synthesis methodology described herein. The $k_{cat}/K_m$ value for the pure substrate in the Der pI assay was measured as $3.5 \times 10^4 M^{-1}s^{-1}$, and was considered to be suitably high for use in a high throughput assay for the general screening of inhibitors of Der pI.

High Throughput Assay Development

Plate assays were carried out in 96 well plate format, using 0.1 ug of Der pI per 100 μL assay volume in each well and using 20 μM of the substrate. All assays were performed in Assay Buffer (AB; 50 mM potassium phosphate, pH 8.25 containing 1 mM ethylenediaminetetraacetic acid (EDTA) and 1 mM dithiothreitol (DTT). The Der pI enzyme is pre-activated by addition of DTT and this in incubated at room temperature for 5 min. prior to initiation of the assay. As an example for the screening methodology, each well contains a 5 μL of a 20 μM solution of the test compound in DMSO, 10 μL of a 200 μM aqueous solution of the substrate, 2, and 85 μL of Der pI in AB is added to initiate the reaction. Enzyme activity is monitored by fluorescence using 320 nm for excitation and 420 nm for the emission wavelengths using a Labsystems Fluroskan Ascent machine. Kinetic measurements were carried out using a Hitachi F-4500 Fluorescence Spectrophotometer.

Synthesis of Inhibitors of Der pI

The best substrate described above was shown by HPLC-mass spectroscopic analysis of the enzyme/assay solution, to be cleaved between the Norleucine-Serine amide bond. Replacement of the terminal Abz group by a series of derivatives (e.g. Boc-, Pivaloyl, Benzoyl, and 2-carboxy-Benzoyl) affected substrate activity and specificity for the Der pI enzyme. With this knowledge of the $P_1$-$P_1'$ cleavage site and for the $P_4$-$P_3$-$P_2$-$P_1$ motif, the compound Boc-Val-Ala-Leu-H, 4, was synthesised as shown in Scheme 1a, FIG. 15.

Figure 16:
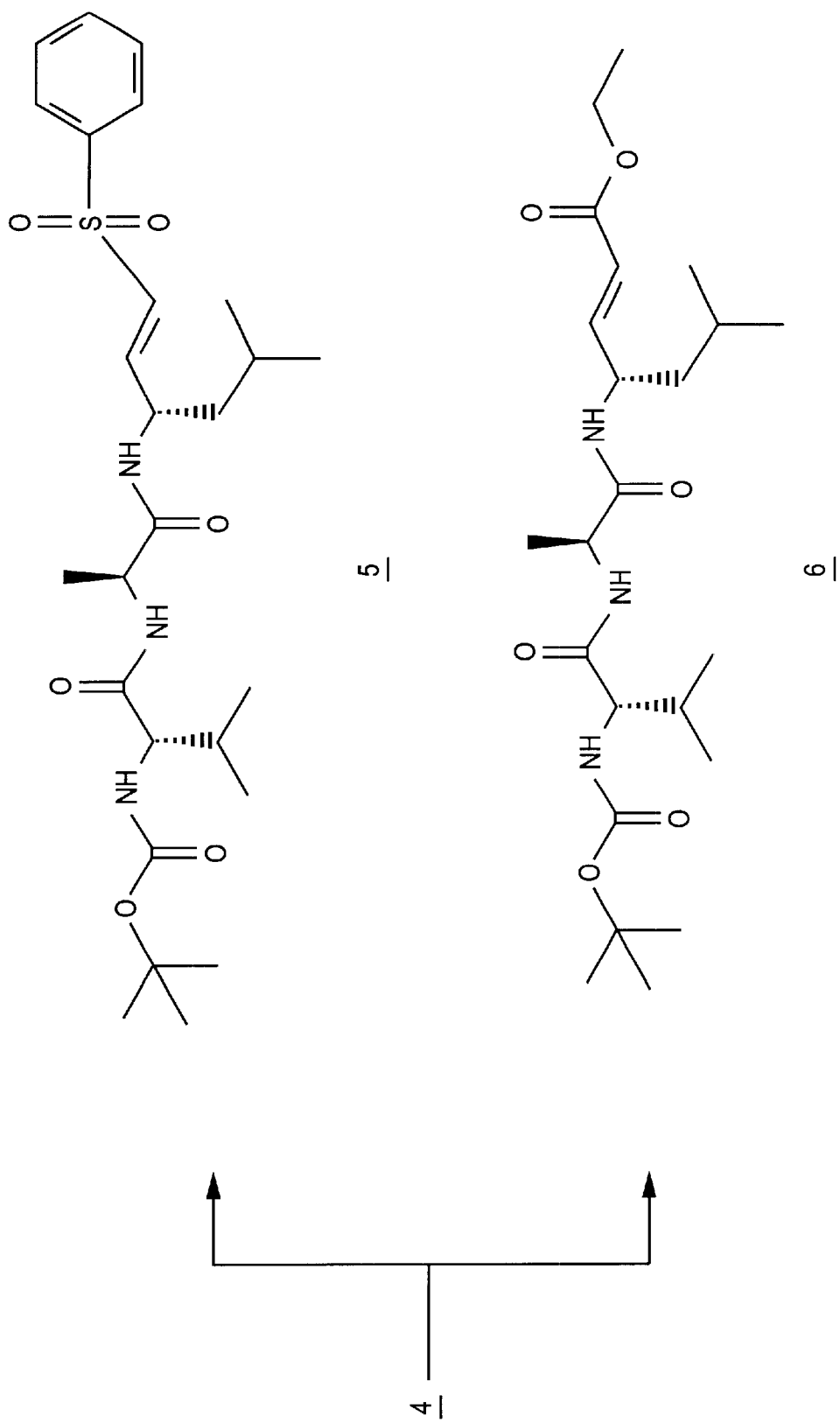
FIG. 16 illustrates a reaction scheme for production of active inhibitors of Der PI.

Attachment of a suitable Michael acceptor such as CH=CH—CO2Et, and —CH=CH—SO$_2$ Ph to the motif (Scheme 2, FIG. 16), provided active inhibitors of the enzyme with apparent IC$_{50}$ values of 50 nM, 1000 nM and 100 nM respectively.

Preparation of an Acyloxymethylketone Series

A series of acyloxymethylketone compounds having active Der PI inhibitor activity was prepared by the following procedures SEQ ID no:86:
N-Benzoyl-L-valyl-L-alanyl-L-norleucine
N-Benzoyl-L-valyl-L-alanyl-L-norleucine SEQ ID no:86 was prepared by solid phase benzoylated peptide synthesis as follows:

Resin Loading (Step 1)

2-Chlorotritylchloride resin (4.9 g, 1.05 mmol/g, Novabiochem) was swelled in dichloromethane (40 ml) and a suspension of Fmoc-L-norleucine added and stirred for 5 minutes. A solution of diisopropylethylamine in DCM(10 ml, 57 mmol in 30 ml) was added over 5 minutes and the resulting mixture stirred at room temperature for 2 hours. Methanol (5 ml) added and reaction mixture stirred for a further 10 minutes before resin filtered and washed with 3×DCM, 2×DMF, 2×2-propanol, 2×DMF, 2×2-propanol, methanol, 2×ether and dried under vacuum for 24 hours.

Amino Acid Deprotection (Step 2)

Fmoc-L-norleucine loaded resin was deprotected by treatment with 20% piperidine in DMF over 4 hours. The swollen resin was filtered, washed with 5×DMF, 2×ether and dried under vacuum for 24 hours.

Peptide Chain Extension (Step 3)

L-Norleucine loaded resin (5 mmol) was added to a solution of Fmoc-L-alanine (6.23 g, 20 mmol), hydroxybenzotriazole (3.0 g, 20 mmol), 2-(1-H-benzotriazole-1-yl)-1,1,3,3-tetramethyluronium hexafluorophosphate (7.59 g, 20 mmol) and diisopropylethylamine (6.97 ml, 40 mmol) in DMF (20 ml) and allowed to swell over 4 hours with mild agitation. Resin was filtered and washed with 4×DMF, 2×ether and dried under vacuum overnight.

Steps (2) and (3) were carried out repetitively with Fmoc-L-alanine and Fmoc-L-valine to afford resin bound tripeptide H-L-valyl-L-alanyl-L-norleucine.

Peptide Chain Benzoylation (Step 4)

L-Valyl-L-alanyl-L-norleucine loaded resin (1 g, approx. 1 mmol) was added to a solution of benzoic acid (0.488 g, 4 mmol), hydroxybenzotriazole (0.6 g, 4 mmol), 2-(1-H-benzotriazole-1-yl)-1,1,3,3-tetramethyluronium hexafluorophosphate (1.52 g, 4 mmol) and diisopropylethylamine (1.40 ml, 8 mmol) in DMF (5 ml) and allowed to swell over 6 hours with mild agitation. Resin was filtered and washed with 4×DMF, 2×ether and dried under vacuum overnight.

Resin Cleavage (Step 5)

N-Benzoyl-L-valyl-L-alanyl-L-norleucine SEQ ID no:86 loaded resin (1.0 g, approx. 1 mmol) was treated with a 1% solution of trifluoroacetic acid in dichloromethane (20 ml) containing triethylsilane (320 ml, 2 mmol) for 1 hour. Resin was removed by filtration and washed with dichloromethane (3×10 ml). Organic layer was collected, evaporated and titrated with ether to afford SEQ ID no:86 N-benzoyl-L- valyl-L-alanyl-L-norleucine (285 mg). Electrospray-MS m/z 407 [MH$^+$].

Bromomethylketone Formation (Step 6) SEQ ID no:87

N-Benzoyl-L-valyl-L-alanyl-L-norleucine bromomethyl ketone N-Benzoyl-L-valyl-L-alanyl-L-norleucine SEQ ID no:86 (140 mg, 0.34 mmol) was suspended in dry THF(3 ml) and dry DMF was added dropwise to afford homogeneity. The reaction mixture was cooled to −10° C. and isobutylchloroformate (129 ml, 1.0 mmol) and N-methylmorpholine (109 ml,1.0 mmol) added with stirring under Argon. The mixture was stirred for 30 minutes before a solution of diazomethane in ether(5 ml, approx. 2 mmol) was added. The reaction mixture was allowed to warm to room temperature over 1 hour before a 1:1 solution of acetic acid and 50% HBr (1 ml, 3.0 mmol HBr) was added dropwise and stirred for 15 minutes. The organic phase was diluted with ethylacetate (40 ml), washed with water (10 ml), brine (10 ml) and sodium bicarbonate (2×10 ml), dried over MgSO$_4$ solvent removed under vacuum. This afforded an off white solid (152 mg) which could be further purified as required by prep. HPLC. Electrospray-MS m/z 482 [MH$^+$] and 484 [MH$^+$].

Acyloxymethylketone Formation (Step 7) SEQ ID no:88

N-Benzoyl-L-valyl-L-alanyl-L-norleucine 2,6-bis(trifluoromethyl)benzoyloxymethyl ketone A mixture of potassium fluoride (0.1 mmol, 6 mg) and 2,6-bis(trifluoromethyl)benzoic acid (0.066 mmol, 17 mg) in dry DMF (500 ml) was stirred over molecular sieves at room temperature for 5 minutes. A solution of SEQ ID no:87 N-benzoyl-L-valyl-L-alanyl-L-norleucine bromomethyl ketone (0.033 mmol, 16 mg) in dry DMF (500 ml) was added and the reaction mixture stirred for 1 hour. The reaction mixture was passed through a short silica plug and washed with 5% methanol in dichloromethane. Solvent was removed under vacuum and the residue purified using prep. HPLC. Freeze drying afforded (6.4 mg) as a white lyophilisate. Electrospray-MS m/z 660 [MH$^+$].

Similarly the following compounds were prepared: SEQ ID no:89

N-Benzoyl-L-valyl-L-alanyl-L-norleucine 2,6-dimethylbenzoyloxymethyl ketone (Electrospray-MS m/z 552 [MH$^+$]) from of SEQ ID no:87 N-benzoyl-L-valyl-L-alanyl-L-norleucine bromomethyl ketone SEQ ID no:90 and 2,6-dimethylbenzoic acid.

N-Benzoyl-L-valyl-L-alanyl-L-norleucine 2-hydroxybenzoyloxymethyl ketone (Electrospray-MS m/z 540 [MH$^+$]) from of SEQ ID no:87 N-benzoyl-L-valyl-L-alanyl-L-norleucine bromomethyl ketone and 2-hydroxybenzoic acid.

N-Benzoyl-L-valyl-L-alanyl-L-norleucine 2,6-dichlorobenzoyloxymethyl ketone SEQ ID no:91 (Electrospray-MS m/z 592 [MH$^+$] and 594 [MH$^+$])from of SEQ ID no:87 N-benzoyl-L-valyl-L-alanyl-L-norleucine bromomethyl ketone and 2,6-dichlorobenzoic acid.

N-Benzoyl-L-valyl-L-alanyl-L-norleucine benzoyloxymethyl ketone SEQ ID no:92 (Electrospray-MS m/z 524 [MH$^+$]) from of N-benzoyl-L-valyl-L-alanyl-L-norleucine bromomethyl ketone SEQ ID NO:87 and benzoic acid.

N-Benzoyl-L-valyl-L-alanyl-L-norleucine 2,3,4,5,6-pentafluorobenzoyloxymethyl ketone SEQ ID no:93 (Electrospray-MS m/z 614 [MH$^+$]) from of SEQ ID no:87 N-benzoyl-L-valyl-L-alanyl-L-norleucine bromomethyl ketone and 2,3,4,5,6-pentafluorobenzoic acid.

N-Benzoyl-L-valyl-L-alanyl-L-norleucine 1,1-dimethylpropyloxymethyl ketone SEQ ID no:94 (Electrospray-MS m/z 504 [MH$^+$]) from of SEQ ID no:87 N-benzoyl-L-valyl-L-alanyl-L-norleucine bromomethyl ketone and 1,1-dimethylpropanoicacid.

N-Benzoyl-L-valyl-L-alanyl-L-norleucine N(benzyloxycarbonyl)-D-serinyl-(O-tert-butyl)oxymethyl ketone SEQ ID no:95 (Electrospray-MS m/z 697 [MH$^+$]) from of SEQ ID no:87 N-benzoyl-L-valyl-L-alanyl-L-norleucine bromomethyl ketone and N-benzyloxycarbonyl-D-serine-O-tert-butylether.

N-Benzoyl-L-valyl-L-alanyl-L-norleucine N(benzyloxycarbonyl)-D-serineoxy methyl ketone SEQ ID no:96 (Electrospray-MS m/z 641 [MH$^+$])from of SEQ ID no:87 N-benzoyl-L-valyl-L-alanyl-L-norleucine bromomethyl ketone and N-benzyloxycarbonyl-D-serine.

N-Benzoyl-L-valyl-L-alanyl-L-norleucine 2-furanoxy methyl ketone SEQ ID no:97 (Electrospray-MS m/z 514 [MH$^+$])from of SEQ ID no:87 N-benzoyl-L-valyl-L-alanyl-L-norleucine bromomethyl ketone and 2-furan carboxylic acid.

N-Benzoyl-L-valyl-L-alanyl-L-norleucine 2,6-dichlorophenylacyloxy methyl ketone, (Electrospray-Ms m/z 606 [MH$^+$], 608 [MH$^+$]) from of SEQ ID no:87 N-benzoyl-L-valyl-L-alanyl-L-norleucine bromomethyl ketone and 2,6-dichlorophenylacetic acid.

Standard Prep. HPLC conditions were as follows: C4 preparative HPLC system (Vydac, 22×250 mm) eluting at 10 ml per minute a gradient of 5–95% (90acetonitrile (0.1% TFA)) over 30 minutes.

The following compounds were prepared by the techniques and procedures described beneath each named compound.

Preparation of SEQ ID no:99 Ethyl-(S)-(E)-3-((tert-butoxy carbonyl amino valyl alanyl)amino-6-methyl-hept-2-enoate To a suspension of sodium hydride (46 mg, 1.9 mmol) in anhydrous THF (4 ml) cooled to 0° C. was added a solution of triethylphosphonoacetate (420 mg, 1.9 mmol) in THF (2 ml) dropwise over 5 minutes and the mixture stirred until gas evolution ceased. The solution was added dropwise to a solution of BocVAL-CHO (600 mg, 1.56 mmol) in dry THF cooled to −10° C. The reaction mixture was stirred for 1 hour and saturated ammonium chloride (10 ml) was added. A white solid precipitated which was removed by filtration and the filtrate was partitioned between ethyl acetate and water. The organic layer was dried with magnesium sulphate and evaporated to give an oil which was crystallised from acetonitrile water to yield the title compound, 640 mg, 91%.

MS (EI+ve) required (M$^+$(C$_{23}$H$_{41}$N$_3$O$_6$)+1)=456: found (M$^+$+H)=456, ((M$^+$-$^t$BOC)+1)=356 (100%).

Preparation of SEQ ID no:100 (S)-(E)-3-((tert-butoxy carbonyl amino valyl alanyl)amino-6-methyl-hept-2-enoic acid The ethyl ester (455 mg, 1 mmol) was dissolved in dioxane (10 ml) and water added followed by lithium hydroxide (126 mg, 3 mmol). The solution was stirred for 3 hours and 1M HCl aq was added until the pH reached neutrality. The dioxane was removed by rotary evaporation and the pH adjusted to 4 with 1M HCl aq. The title compound precipitated, filtered and washed with water to yield 420 mg, 98%.

MS (EI+ve) required (M$^+$(C$_{21}$H$_{37}$N$_3$O$_6$)+1)=428: found (M$^+$+H)=428 (100%).

Preparation of SEQ ID no:101 1,1,1-Trifluoroethyl-(S)-(E)-3-((tert-butoxy carbonyl amino valyl alanyl) amino-6-methyl-hept-2-enoate The acid (BocVAL-CO$_2$H) (50 mg, 0.117 mmol) and dimethylaminopyridine (29 mg, 0.24 mmol) was dissolved in dry dichloromethane (1 ml) and cooled to 0° C. Water soluble carbodiimide hydrochloride salt (26 mg, 0.13 mmol) in 0.5 ml dichloromethane was added and the solution stirred for 5 minutes. 1,1,1-Trifluoroethanol (0.017 ml, 0.23 mmol) in 0.5 ml dichloromethane was added and the reaction was allowed to warm to room temperature after 1 hour and the reaction mixture stirred overnight. The reaction mixture was washed 2×2 ml 0.5M citric acid solution, 1×2 ml water, 1×2 ml saturated sodium bicarbonate solution, 1×2 ml water, dried with magnesium sulphate and evaporated to dryness to give the title compound.

MS (EI+ve) required $(M^+(C_{23}H_{38}N_3O_6F_3)+1)=510$: found$(M^++H)=510$, $((M^+\text{-}^tBOC)+1)=410$, $((M^+\text{-}^tBu)+1)=454$ (100%).

Preparation of SEQ ID no:102 Ethyl-(S)-(E)-3-(N-benzoyl valyl alanyl)amino-6-methyl-hept-2-enoate The tert-butoxy carbonyl protected ethyl ester (16.6 mg, 0.036 mmol) was dissolved in 4.0 M HCl in dioxane (2 ml) stirred at room temperature for 30 minutes and evaporated to dryness. The residue was dissolved in DMF (0.5 ml) and N-methylmorpholine (7.36 mg, 0.073 mmol) added followed by benzoyl chloride (5.4 mg. 0.038 mmol) in DMF 0.5 ml. The reaction stirred for 2 hours, diluted with 0.1% trifluoroacetic acid solution (4 ml) and acetonitrile (2 ml) and injected onto a C4 preparative HPLC system (22×250 mm) eluting at 10 ml per minute, monitoring at 215 nm and a gradient of 10–90% system B over 25 minutes and holding at 90% for 15 minutes. System A=0.1% TFA in water, system B=90% acetonitrile, 10% system A. The peak eluting at 26–28 minutes was collected and lyophilised to a white solid, yield 4.5 mg, 27%.

Analysis by MS (EI+ve) required $(M^+(C_{25}H_{37}N_3O_5)+1)=460$: found$(M^++H)=460$.

Preparation of Diethyl Phenylsulfonylmethylphosphonate

The Diethyl Phenyl sulfonylmethylphophonate was prepared using a method adapted from I. Shahak, and J. Almog. (*Synthesis*, 145,1970).

The commercially available diethyl phenylthiomethylphosphonate (1.0 ml, 4.1 mmol) was dissolved in dichloromethane (10 ml). Sulphuric acid (10 ml, 25%) was added and the mixture cooled on ice. Solid potassium permanganate was then added in three aliquots of 0.5 g with stirring. After the additions the reaction appeared to be complete. Solid sodium metabisulfite was added slowly until the mixture turned colourless. This was then extracted with ethyl acetate (×3) and the combined organic washings washed with saturated sodium bicarbonate solution followed by brine before drying over sodium sulphate. The volatiles were removed in vacuo. The residue was purified by flash chromatography on silica eluting initially with ethyl acetate/hexane 8/2 followed by pure ethyl acetate.

In this way the desired product, diethyl phenylsulfonylmethylphosphonate (1.0 g, quant) was obtained as a colourless solid.

The product was analysed by mass spectrometry (MS) (MALDI-TOF): required $(M^+(C_{11}H_{17}O_5PS)+1)=292$; obtained $(M^++1)=292$ Preparation of SEQ ID no:103 (S)-(E)-3-((tert-butoxycarbonylaminovalyl)alanyl)amino-1-phenylsulfonyl-5-methyl-1-hexene Diethyl phenylsulfonylmethylphosphonate (38 mg, 129 mmol) was dissolved in dry THF (10 ml) and then cooled to 0° C. under an atmosphere of nitrogen. Sodium hydride (8 mg of 60% dispersion in oil, 200 mmol) was added and the mixture stirred for 15 mins (effervescence). The aldehyde $^t$Boc-Val-Ala-Leu-CHO (50 mg, 129 mmol) was then added to the resulting solution and the mixture was stirred for 60 mins. The reaction was quenched by the addition of dilute hydrochloric acid (0.1 M), followed by extraction with ethyl acetate (×3). The separated organic phase was sequentially washed with saturated sodium bicarbonate solution and brine before drying over sodium sulphate. The volatiles were removed in vacuo. The residue was purified by flash chromatography on silica eluting with ethyl acetate/hexane 4/6. An unidentified by-product-was eluted first (12 mg) followed by the desired product SEQ ID no:103 (S)-(E)-3-((tert-butoxycarbonylamino-valyl)alanyl) aminophenylsulfonyl-5-methyl-1-hexene (22 mg, 32%) as a solid.

MS (electrospray) required $(M^+(C_{26}H_{41}O_6N_3S)+1)=523$: found $(M^++Na)=546$, $((M\text{-}^tBoc)+1)=424$ (100%).

Preparation of Diethyl methylsulfonylmethylphosphonate

The commercially available Diethyl methylthiomethylphosphonate was converted to the title compound using the method of I. Shahak and J. Almog (*Synthesis*, 171, 1969).

Preparation of SEQ ID no:104 (S)-(E)-3-((tert-butoxycarbonylaminovalyl)alanyl)amino-1-methylsulfonyl-5-methyl-1-hexene Diethyl methylsulfonylmethylphosphonate (30 mg, 130 mmol) was dissolved in dry THF (5 ml) and then cooled to 0° C. under an atmosphere of nitrogen. Sodium hydride (7 mg of 60% dispersion in oil, 175 mmol) was added and the mixture stirred for 15 mins (effervescence). The aldehyde $^t$Boc-Val-Ala-Leu-CHO (50 mg, 129 mmol) was then added to the resulting solution and the mixture then stirred for 60 mins. The reaction was quenched by addition of dilute hydrochloric acid (0.1 M), followed by extraction with ethyl acetate(×3). The separated organic phase was sequentially washed with saturated sodium bicarbonate solution and brine before drying over sodium sulphate. The volatiles were then removed in vacuo. The residue was purified by flash chromatography on silica eluting with ethyl acetate/hexane 8/2. An unidentified by-product was eluted first (4 mg), followed by the desired product SEQ ID no:104 (S)-(E)-3-((tert-butoxycarbonylamino-valyl)alanyl) aminomethylsulfonyl-5-methyl-1-hexene (24 mg, 40%) as a solid.

MS (electrospray) required $(M^+(C_{21}H_{39}O_6N_3S)+1)=462$: found $(M^++Na)=484$, $((M\text{-}^tBoc)+1)=362$ (100%).

Preparation of Ethyl diethylphosphorylmethylsulfonate

Prepared in accordance with procedure B described in L. Ghosez et. al. (*Tetrahedron*, 43, 5125, 1987).

The product was analysed on MS (electrospray) required $(M^+(C_7H_{17}O_6PS)+1)=261$: Found $(M^++H)=261$, $(M^++Na)=283$.

Preparation of SEQ ID no:105 Diethyl(S)-(E)-3-(tert-butoxycarbonylamino-valyl)alanyl)amino-5-methylhexenylsulfonate Ethyl diethylphosphorylmethanesulfonate (36 ml, ~138 mmol) was dissolved in dry THF (5 ml) and then cooled to 0° C. under an atmosphere of nitrogen. Sodium hydride (8 mg of 60% dispersion in oil, 200 mmol) was added and the mixture stirred for 15 mins (effervescence). The aldehyde 'Boc-Val-Ala-Leu-CHO (50 mg, 129 mmol) was added to the resulting solution and the mixture stirred for 30 mins.

The reaction was quenched by addition of dilute hydrochloric acid (0.1 M), followed by extraction with ethyl acetate (×3). The separated organic phase was sequentially washed with sodium bicarbonate solution and brine before drying over sodium sulphate. The volatiles were then removed in vacuo. The residue was purified by flash chromatography on silica eluting with ethyl acetate/hexane 1/1. The desired product SEQ ID no:105 Diethyl(S)-(E)-3-((tert-butoxycarbonylamino-valyl)alanyl)amino-5-methylhexenylsulfonate, (22 mg, 35%) was obtained as a solid.

MS(electrospray) required($M^+(C_{22}H_{41}O_7N_3S)+1$)=492: found ($M^++1$)=492, (($M^+$-'Boc)+1)=392 (100%)

Example 2

Design of Depsipeptides

Another suitable bond in a compound of general formula (I), (II) or (III) according to the invention is an ester bond to form a depsipeptide. The incorporation of depsipeptide substrates aided the identification of substrates for low reactivity viral proteases, such as viral serine proteases.

For example, substrates of the general formula

$n$[Abz-$B_{1-10}$-$C_{1-10}$-$D_{1-8}$y[COO]-$E_{1-8}$-Tyr(NO$_2$)-Asp-NH$_2$]

were produced.

However, a significant proportion of viral proteases only recognise substrate sequences larger than those represented by the general structure above. It is well acknowledged that by the very nature of action of a viral protease (function is to cleave immature viral proteins into the mature viral package) one automatically receives data concerning the natural substrate sites. Thus, the general structure above can be extended by introducing extra fixed amino-acids at appropriate sites. A logical extension would be to introduce the known P1-P1' cleavage site as the depsipeptide bond, then subsequently introduce the four variant positions following the standard format thus;

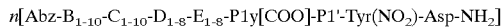

$n$[Abz-$B_{1-10}$-$C_{1-10}$-$D_{1-8}$-$E_{1-8}$-P1y[COO]-P1'-Tyr(NO$_2$)-Asp-NH$_2$]

Furthermore, if these substrates again proved to be too small, one may use the known substrate sequences to introduce additional fixed positions. For instance, with Hepatitis NS3 protease it is known that the natural P6 position is a conserved acidic residue (aspartic or glutamic acid). Thus one could extend the above structure as detailed below.

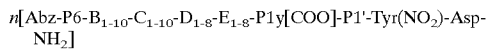

$n$[Abz-P6-$B_{1-10}$-$C_{1-10}$-$D_{1-8}$-$E_{1-8}$-P1y[COO]-P1'-Tyr(NO$_2$)-Asp-NH$_2$]

The novel methodology described herein greatly facilitates the invention of therapeutically useful proteolytic enzyme inhibitors and is commercially exploitable. This is because the best substrate motif for the proteolytic enzyme can be rapidly identified, and, since there exist in the literature a variety of ways for attaching motifs which react with the active site of a proteolytic enzyme, especially for aspartyl, metallo, serine and cysteinyl proteases, an enzyme inhibitor can be readily synthesised. Moreover, amide bond replacements or transition state mimetics can be incorporated into the molecule, which would be especially useful for the inhibition of aspartyl or metallo proteases.

The method described also facilitates the rapid development of a screening assay for novel protease inhibitors. The most potent fluorogenic substrate discovered by library screening can subsequently be used for the detection of inhibitors of the particular proteolytic enzyme under scrutiny.

The presence of an inhibitor within the compound libraries described is readily detected by retreatment of the assay mixture with the most active fluorogenic substrate, which will allow the immediate measurement of the remaining proteolytic enzyme activity.

The invention provides self-decoding, combinatorial fluorogenic libraries, and it will greatly facilitate the design and invention of novel protease inhibitors because:

i. The peptides of the library may have increased aqueous solubility in comparison to peptides containing similar and other fluorogenic and quencher groups.

ii. The peptides are stable to contaminating exopeptidases.

iii. The self deconvolution-method described, coupled with the continuous analysis of the rate of substrate cleavage data, allows the immediate identification of the most active binding motif contained within the substrate library.

iv. The method allows for the rapid assessment of the enzyme assay mixture for any compounds in the library that are acting as enzyme inhibitors.

ABBREVIATIONS

Abbreviations used herein are as follows:

Abbreviations for amino acids and nomenclature of peptide structures follow the recommendations given in: IUPAC-IUB Commission on Biochemical Nomenclature, (*J. Biol. Chem*, 247, 997, 1971). All chiral amino acids are of the L configuration unless otherwise stated. Other abbreviations used are:

-Abu , b-amino butyric acid, :Abz, 2-amino benzoyl:ACH, 1-amino-1-carboxy-cyclohexane:ACP, 1-amino-1-carboxycyclopropane:Bip, Biphenylalanine:n-Bu, n-butoxycarbonyl:Bz, Benzoyl:Bz(2-carboxy), 2-carboxybenzoyl:Bu$^t$Gly, tert-Butylglycyl:BOP, benzotriazoyl-oxy-tris-(dimethylamino)-phosphonium hexafluorophosphate:Cha, cyclohexylalanine:Chex, 1-carboxycyclohexyl:eAHA, gamma aminchexanoyl:HBTU, O-benzotriazoyl-N,N,N',N'-tetramethyluronium hexafluorophosphate:HOBt, 1-hydroxybenzotriazole:Hyp, trans-4-hydroxyprolinyl:hLeu, homoleucyl:2Nal, 2-napthylalanine:NMM, N-methylmorpholine:Piv, pivoyl:3pyr, 3-pyridylalanine:Tic, 2-carboxytetrahydroquinolyl:Tyr(NO$_2$), 3-nitrotyrosine.

DMF, dimethylformamide; Fmoc, fluorenylmethoxycarbonyl; HPLC, high performance liquid chromatography; Pfp, pentafluorophenyl, tBoc, tert-butoxycarbonyl; tBu, tert-butyl; TFA, trifluoroacetic acid; Pmc, pentamethyl chroman, Pbf, pentamethylbenzofuran, TBTU, 2-(1H-Benztrotriazole-1-yl)-1,1,1,3,3-tetramethyluronium tetrafluoroborate; Trt, Trityl.

p.Aba, 4-aminobenzoyl; Aib, Aminoisobutyric acid; Bip, Biphenylalanine; nBu, n-Butyl; Bz, Benzoyl; Cmpi, Carboxymethylpiperazine; Deg, Diethylglycine; DIPEA, N,N-Diisopropyl-ethylamine; HATU, O-(7-azabezotriazol-1-yl)-1,1,3,3-tetramethyluronium hexafluorophosphate; HOAT, 1-hydroxy-7-azabenzotriazole; Naph, Naphthylalanine; 3.Pyr, 3-pyridiylalanine; Tyr(NO$_2$), 3-nitro-tyrosine.

REFERENCES

1. I. Schlechter and A. Berger, Biochem. Biophys. Res. Commun., 1967, 27, 157–162)
2. A. Carmel et al., FEBS Lett., 1973, 30, 11.
3. M. M. Meldal and I. Svendsen, J. Chem. Soc. Perkin Trans.1, 1995, 1591–1596,
4. M. Meldal and K. Breddam, Anal. Biochem., 1991, 195, 141–147,
5. T. Forster, Ann. Phys., 1948, 6, 55.
6. A. Yaron, A. Carmel, and E. Katchalski-Katzir, Anal. Biochem. 1979, 95, 228 and references therein.
7. S. A. Latt et al., Anal. Biochem., 1972, 50, 56.
8. A. Persson et al., Anal. Biochem., 1977, 83, 2,96.
9. I. Yu Filppova et al., Bioorg. Khim., 1986, 12, 1172.
10. J. Pohl et al., Anal. Biochem., 1987, 165, 96.
11. S. J. Pollack et al., J. Am. Chem. Soc., 1989, 111, 5961.
12. E. K. Bratovanova and D. D. Petkov, Analytical Biochem., 1987, 162, 213.
13. J. Singh et al., J. Med. Chem., 1995, 38, 217–219 and references therein.
14. M. Green et al. in 'Innovation and Perspectives in Solid Phase Synthesis' (R. Epton Ed.) Mayflower Worldwide Ltd., Birmingham., UK. 1994, 239–244.
15. J. R. Petithory et al., Proc. Natl. Acad. Sci. USA, 1991, 88, 11510–11514
16. J. Berman et al., J. Biol. Chem., 1992, 267, 1434–1437.
17. H. Drevin, A, -T. Martin, J. Carlsson, S. Oscarsson, T. Lovgren, I. Hemmila and M. Kwiatkowski, WO89/10975, (May 5, 1988)
18. A. J. Garman and N. G. Phillips, WO 94/28166 (May 27, 1993)
19. G. T. Wang and E. D. Matayoshi, E.P. 428000 (Nov. 3, 1989)
20. G. A. Krafft, G. T. Wang and E. D. Matayoshi, EP 428000, (Nov. 3, 1989).
21. G. R. Marshall and M. V. Toth, U.S. Pat. No. 5,164,300, (Dec. 11, 1990).
22. G. R. Marshall and M. V. Toth, U.S. Pat. No. 5,011,910, (Dec. 28, 1989).
23. K. T. Chapman, N. A. Thornberry, M. Maccoss, J. R. Weidner, R. A. Mumford, W. K. Hagmann, EP 528487A (Aug. 16, 1991)
24. R. P. Haugland, WO 93/04077, (Aug. 23, 1991)
25. R. M. Valerio, A. M. Bray N. J. Maeji, Int. J. Peptide Protein Res., 1994, 44, 158–165
26. M. Bastos, N. J. Maeji and R. H. Abeles, Proc. natl. Acad. Sci., 1995, 92, 6738–6742.
27. 'Solid Phase Peptide Synthesis', E. Atherton and R. C. Sheppard, IRL Press 1989.

---

What is claimed is:

1. A method for screening for proteolytic activity of an enzyme applied to wells of a wellplate on one or more compounds of FRET compound mixtures applied to the wells, wherein the FRET compound mixtures define a complementary pair of compound libraries wherein the activity is the interaction of proteolytic enzyme applied to a well with one or more compounds of a mixture in the well, wherein the interaction represents cleavage of the compound by the enzyme, using a complementary pair of compound libraries L1 and L2 which constitute a set containing combinatorial fluorescence resonance energy transfer (FRET) compounds of formula:

$$Aa\text{-}Bb\text{-}Ce\text{-}Dd\text{-}n(Ee)\text{-}Ff\text{-}Gg$$

in which;

A represents a fluorescor internally quenched by F;

B, C, D, and E represent natural or unnatural amino acid groups such that the scissile bond between any two of these groups is an amide bond;

F represents a quencher capable of internally quenching the fluorescor A;

G which is optionally present is a hydrophilic moiety imparting solubility on the compound;

and wherein all compounds are in aqueous solution; and n represents an integer between 1 and 4 inclusive;

giving $a \times b \times c \times d \times e \times f \times g = M^n$ compounds in each library, there being a predetermined number (P1, P2) of mixtures each consisting of a predetermined number (Q1, Q2) of individual identifiable compounds in each library, wherein both L1 and L2 contain the same $M^n$ compounds, but wherein any two compounds which are found together in one mixture of Q1 compounds of L1 are not found together in any one of the P2 mixtures of L2 in which the P1 mixtures of L1 and the P2 mixtures of L2 are each placed separately into individual wells of well plates, the well plates having wells arranged in a format adapted to allow deduction of a unique active compound formula from the presence or inhibition of proteolytic activity in one well of L1 and one well of L2, wherein the format complies with general deconvolution formulae in which:

(i) ns=Rp.Cp.Rs.Cs.np (ii) k=b.c.d.np.e (iii) k=x.N.np (iv) N=Rp.Cp (v) K=X.Rp.Cp.np (vi b.c.d.e=X.Rp.Cp vil) Cp.e=X (viii) Rp.e=X, if Rp=Cp and wherein a, b, c, d, a, t and g are represent the number of species of A, B, C, D, E, F and G, respectively, within each library np=number of primary plates ns=number of secondary plates Rp=number of primary rows Rs=number of secondary rows Cp=number of primary columns Cs=number of secondary columns
K=number of combinations of compounds
N=number of wells on a plate, and
X=number of compounds per well.

2. A method according to claim 1 wherein np=4
ns=16
Rp=8
Rs=4
Cp=10
Cs=5
K=6400
N=80
X=20.

3. A method according to claim 1 wherein the complementary library pair has the scissile bond between D and E.

4. A method according to claim 1 wherein A represents an unsubstituted or substituted anthranilic acid derivative.

5. A method according to claim 1, wherein F represents an unsubstituted or substituted 3-nitrotyrosine derivative.

6. A method according to claim 1 in which G represents an aspartyl amide moiety.

7. A method according to claim 1 wherein each of the complementary libraries comprises 1600n compounds as 80n mixtures of 20 distinct, identifiable compounds.

8. A method according to claim 1, further comprising the additional step of identifying an enzyme inhibitor or inhibitors wherein a FRET compound which has been identified as a substrate by the method of claim 2 is used in an inhibition assay with the enzyme separately against a panel of possible inhibitors.

9. A method according to claim 1 wherein the compounds of the library pair are synthesized using a solid phase technique.

10. A method according to claim 1, further comprising the subsequent step of identifying the presence of enzyme inhibitors within said mixtures, the method comprising quantifying the enzymatic activity remaining in each well following said applying of the complementary libraries to said wells.

* * * * *

UNITED STATES PATENT AND TRADEMARK OFFICE
CERTIFICATE OF CORRECTION

PATENT NO.   : 6,528,275 B1
DATED        : March 4, 2003
INVENTOR(S)  : Quibell et al.

It is certified that error appears in the above-identified patent and that said Letters Patent is hereby corrected as shown below:

<u>Title page,</u>
Item [73], Assignee, please delete "Peptide Therapeutics Limited, Cambridge (GB)" and insert -- Medivir UK Limited, Cambridge (GB) --.

Signed and Sealed this

Twentieth Day of January, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,528,275 B1
APPLICATION NO. : 09/171,680
DATED : March 4, 2003
INVENTOR(S) : Quibell et al.

Page 1 of 1

It is certified that error appears in the above-identified patent and that said Letters Patent is hereby corrected as shown below:

Column 14, line 1, replace "/Rs.Cs.np" with --.np/(Rs.Cs)--;
        line 6, replace the equation with --ns = 8 x 10 .np/(4 x 5) = 16 plates--;
        line 40, replace "cp" with --Cp--.

Claim 1, lines 25 and 29, replace "$M^n$" with --M$n$--;
        line 41, replace "Rs.Cs.np" with --.np/(Rs.Cs)--;
        line 43, replace "x" with --X--;
        line 45 and 58, replace "K" with --k--.

Claim 2, line 8, replace "K" with --k--.

Signed and Sealed this

Seventeenth Day of April, 2007

JON W. DUDAS
*Director of the United States Patent and Trademark Office*